(12) United States Patent
Cuddy et al.

(10) Patent No.: US 11,771,514 B1
(45) Date of Patent: Oct. 3, 2023

(54) CONTAINERS AND METHODS FOR TISSUE STORAGE DURING SURGERY

(71) Applicant: Clinical Biotechnology Research Institute at RSFH, Charleston, SC (US)

(72) Inventors: Brian G. Cuddy, Charleston, SC (US); Byron N. Bailey, Sullivans Island, SC (US); Andrea H. Marshall, Mt. Pleasant, SC (US); Jill N. Nichols, North Charleston, SC (US)

(73) Assignee: Clinical Biotechnology Research Institute at RSFH, Charleston, SC (US)

(*) Notice: Subject to any disclaimer, the term of this patent is extended or adjusted under 35 U.S.C. 154(b) by 0 days.

(21) Appl. No.: 17/000,392

(22) Filed: Aug. 24, 2020

Related U.S. Application Data

(60) Provisional application No. 62/890,318, filed on Aug. 22, 2019.

(51) Int. Cl.
*A61B 50/30* (2016.01)
*A61B 50/00* (2016.01)

(52) U.S. Cl.
CPC ........ *A61B 50/30* (2016.02); *A61B 2050/005* (2016.02); *A61B 2050/3008* (2016.02)

(58) Field of Classification Search
CPC .............. A61B 50/30; A61B 2050/005; A61B 2050/3008; B65D 5/48; Y10T 24/1394;
(Continued)

(56) References Cited

U.S. PATENT DOCUMENTS 4,928,823 A * 5/1990 Campbell .............. A45C 13/02
206/338
5,127,537 A 7/1992 Graham
(Continued)

FOREIGN PATENT DOCUMENTS

| EP | 0665424 A1 | 8/1995 |
|---|---|---|
| WO | 02/18210 A1 | 3/2002 |
| WO | 2018/151809 A1 | 8/2018 |

OTHER PUBLICATIONS

International Search Report for PCT/US2018/000019 dated Jun. 27, 2018 (3 pages).
(Continued)

*Primary Examiner* — Steven A. Reynolds
(74) *Attorney, Agent, or Firm* — Thrive IP®; Jeremy M. Stipkala; William La Salle, III

(57) ABSTRACT

Containers and methods protect surgically-removed tissue such as cranial bone flaps for limited times during surgery. In some cases, tissue protected in such a container can be returned to the patient, lessening the need for synthetic, allographic, or xenographic alternatives. A container may include a frame defining a plurality of retention compartments, each retention compartment having an orientation and comprising sidewalls supported by the frame, wherein the sidewalls define a rim for each retention compartment in the plurality of retention compartments, wherein the orientation of a first retention compartment in the plurality of retention compartments differs from the orientation of a second retention compartment in the plurality of retention compartments.

18 Claims, 15 Drawing Sheets

(58) Field of Classification Search
CPC ............... A45F 5/021; A45F 2005/026; A45F 2005/025
USPC ........... 206/570, 438; 220/503, 504; 24/3.12
See application file for complete search history.

(56) References Cited

U.S. PATENT DOCUMENTS

| | | | | |
|---|---|---|---|---|
| 5,547,080 | A * | 8/1996 | Klimas | B25H 3/02 |
| | | | | 182/129 |
| 5,609,827 | A | 3/1997 | Russell et al. | |
| 6,540,084 | B2 * | 4/2003 | Silvers | B65D 51/28 |
| | | | | 206/494 |
| 7,124,883 | B1 * | 10/2006 | Thomas | B65D 43/162 |
| | | | | 206/256 |
| 8,333,310 | B2 * | 12/2012 | Tages | A45F 5/02 |
| | | | | 224/668 |
| 8,584,916 | B1 * | 11/2013 | Chen | A45F 5/021 |
| | | | | 224/904 |
| 2005/0006268 | A1 * | 1/2005 | Futernick | B65D 25/22 |
| | | | | 206/518 |
| 2005/0194391 | A1 | 9/2005 | Domke et al. | |
| 2011/0308973 | A1 | 12/2011 | Patenaude | |

OTHER PUBLICATIONS

Written Opinion for PCT/US2018/000019 dated Jun. 27, 2018 (8 pages).

* cited by examiner

© 2019 CBRI

© 2019 CBRI

© 2019 CBRI

FIG. 16   © 2020 CBRI

© 2020 CBRI

CONTAINERS AND METHODS FOR TISSUE STORAGE DURING SURGERY

CROSS-REFERENCE TO RELATED APPLICATIONS

The present application claims benefit of priority under 35 U.S.C. § 119(e)(1) to U.S. Provisional Patent Application No. 62/890,318, filed on Aug. 22, 2019, and entitled, "CONTAINERS AND METHODS FOR TISSUE STORAGE DURING SURGERY." The '318 application is incorporated herein by reference in its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

The present invention relates to protecting a surgically removed medical tissue sample from contamination, damage, or loss during a medical procedure by placing the medical tissue sample in a sterile container with distinguishing characteristics and a closure device.

BACKGROUND OF THE INVENTION

In surgical and emergent medical procedures, it often becomes necessary to set aside tissue that will be reused in a patient. For example, in a craniotomy, a cranial bone flap can be removed and set aside, only to be returned to the patient near the conclusion of the procedure. In another example, tissue from one part of a patient's body is removed for a brief time, and grafted to another part of the patient's body, such as, for example, for facial or breast reconstruction, coronary bypass surgery, correction of receding gums, or for various types of grafts. In still another example, traumatic injuries can result in the near-amputation of, for example, fingers, toes, and ears. It may be desirable in a given case to temporarily remove the injured tissue from the patient, clean and prepare the wound, and then regraft the injured tissue to the prepared wound. A regrafted ear, for example, can save a patient from disfigurement and the risks associated with transplanting a synthetic, allographic, or xenographic substitute.

A craniotomy will be used to illustrate one device of the invention and its use. During a craniotomy, a section of the skull, called a bone flap, is removed to access the brain underneath. The skin and muscles are lifted off the bone and folded back, and small burr holes are made in the skull with a drill. A special saw is inserted through the burr holes, and is used to cut the outline of a bone flap. The cut bone flap is lifted and removed to expose the protective covering of the brain called the dura. Typically the bone flap is safely stored until it is replaced at the end of the procedure.

Once the repair of the underlying tissues is complete, the dura is closed with sutures. The bone flap is replaced back in its original position and secured to the skull with titanium plates and screws. The muscles and skin are sutured back together.

There are several known methods for preserving a cranial bone flap for extended storage periods, but methods for storing bone flaps for a shorter time period, such as during a craniotomy, presents a difficult and unmet challenge. The long term storage options may be required in the event of a craniectomy, where the bone flap is not replaced during the surgical event. These long term storage options may include placing the bone under the subcutaneous abdominal tissue, preservation of bone in the subgaleal space on the edges of the craniotomy, freezing of the bone flap as referenced in U.S. Pat. No. 8,382,844, and discarding the flap and replacing with a synthetic material.

In the event of shorter term storage, such as that required during the period of a surgical procedure, there is a need to safely store a medical tissue sample during the surgical procedure. One current practice in the operating room is to store the bone flap in a moistened laparotomy pad, or some other container that is commonly found in a sterile surgical procedure pack. As the surgery nears completion, the bone flap is removed from the laparotomy pad for reattachment to the skull.

The sterile surgical procedure pack referenced above is illustrated in U.S. Pat. No. 4,844,259, and discloses use of surgical procedure packs for the surgical removal of a medical tissue sample and a packaging means for long term storing and transporting said sample. This reference does not disclose a device or method to use for short term storage during a surgical procedure, nor try to solve the problem of safeguarding the medical tissue sample during the surgical procedure.

There are several disadvantages to storing a bone flap in the aforementioned laparotomy pad. The laparotomy pad may become blood soaked and can be misplaced or mixed in with similar pads, or can be inadvertently dropped on the floor, exposing the bone flap to damage or contamination. Since the laparotomy pad does not contain any markings that indicate the contents of the pad, or colors to distinguish it from other pads, it blends in with other materials and pads on a surgical tray or surgical table. Due to these conditions, it is likely that the laparotomy pad containing the bone flap could be mixed in with other pads in the operating room which may cause confusion or inadvertent damage to the human tissue that is important for a successful surgical closure. This could result in surgical time delays to look for the lost or misplaced laparotomy pad that contains the bone flap. It is also likely that the pad could be inadvertently picked up or moved, causing the bone flap to fall out of the laparotomy pad and onto the floor, which is an unsterile environment. At a minimum, this could contaminate the bone flap, resulting in the need for cleaning, which would add time to the surgical procedure. In a worst case scenario, this could cause damage to the bone, resulting in the need to create a synthetic replacement, which would increase the time the patient is under sedation.

Another disadvantage to storing a bone flap in the aforementioned laparotomy pad is that the laparotomy pad containing the bone flap may be mistakenly thrown away or discarded during surgery. If this is not detected, this will result in the need for a synthetic implant with the same issues as noted above.

SUMMARY OF THE INVENTION

Unexpectedly, Applicants have invented devices and methods for storing tissue during surgery or other medical procedures, or for short durations. Some embodiments of the present invention provide containers for storing a tissue sample during a medical procedure, one such container comprising of a frame defining a plurality of retention compartments, each retention compartment having an orientation and comprising sidewalls supported by the frame wherein the sidewalls define a rim for each retention compartment in the plurality of retention compartments wherein the orientation of a first retention compartment in the plurality of retention compartments differs from the orientation of a second retention compartment in the plurality of retention compartments.

Other embodiments relate to methods of storing a tissue sample(s) during a medical procedure, one such method comprising a plurality of lids, one lid for each retention compartment in the plurality of retention compartments; wherein each lid in the plurality of lids comprises a seal adapted to impermeably engage the rim of a retention compartment in the plurality of retention compartments; and an anchor permanently affixing the lid to the frame proximal to the retention compartment in the plurality of retention compartments.

Further embodiments provide a stabilizing structure adjustably affixed to the frame and adapted to stabilize the container in the orientation of at least one retention compartment in the plurality of retention compartments.

Additionally, other embodiments provide a method of storing a tissue sample during a medical procedure, comprising of obtaining the container described and placing the tissue sample(s) into one or more retention compartments in the plurality of retention compartments, impermeably engaging the seal of the lid associated to that retention compartment(s) containing the tissue sample(s) and storing the tissue sample(s) in the container for a short duration, typically no more than 48 hours.

Still, other embodiments provide a method of storing an implantable device, prior to or during a medical procedure, comprising of obtaining the container described and placing the implantable device(s) into one or more retention compartments in the plurality of retention compartments, impermeably engaging the seal of the lid associated to that retention compartment(s) containing the implantable device(s) and storing the implantable device(s) in the container for a short duration, typically no more than 48 hours.

While the disclosure provides certain specific embodiments, the invention is not limited to those embodiments. A person of ordinary skill will appreciate from the description herein that modifications can be made to the described embodiments and therefore that the specification is broader in scope than the described embodiments. All examples are therefore non-limiting.

DETAILED DESCRIPTION

Figure 1:
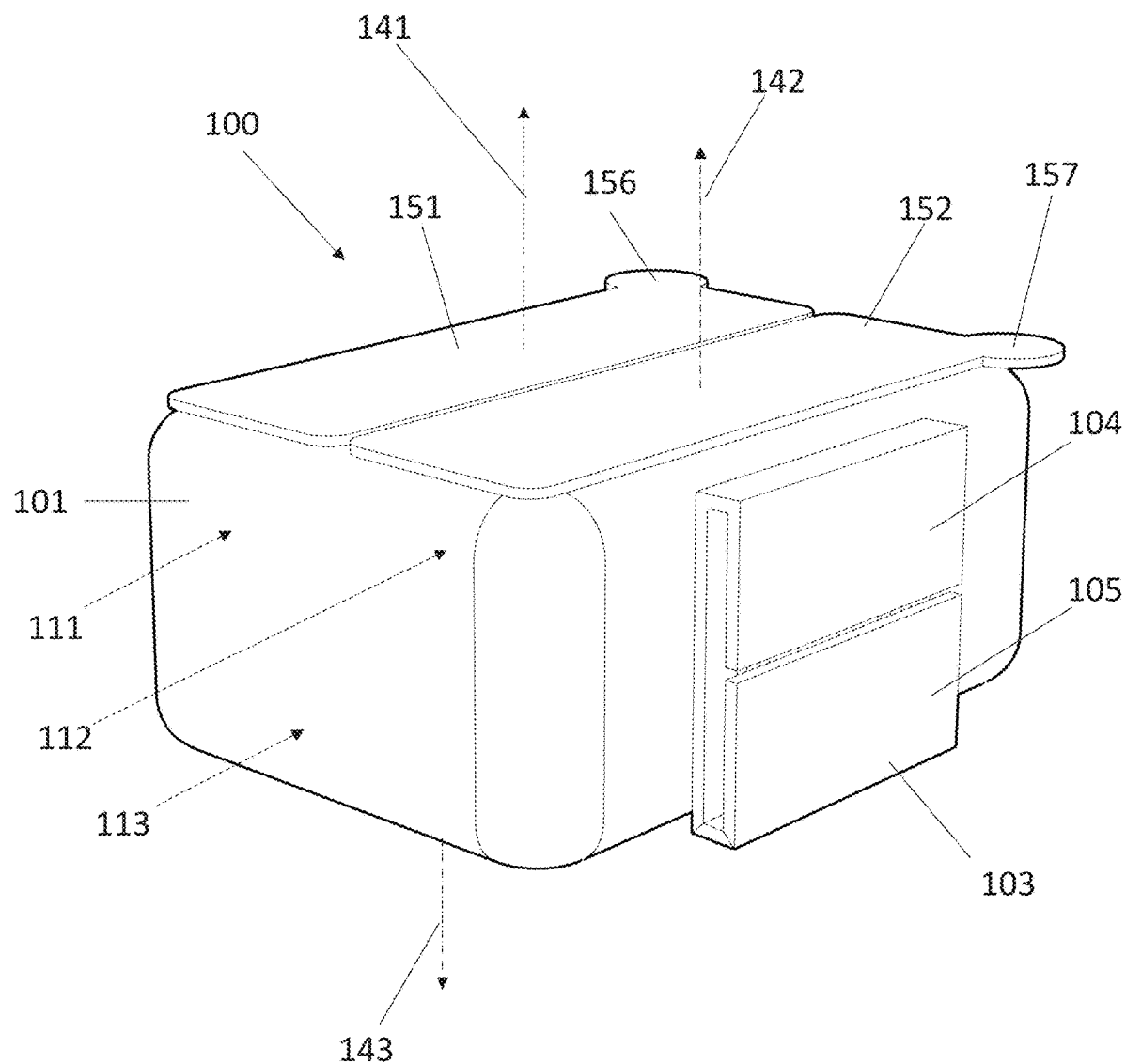
FIG. 1 depicts one embodiment of the invention comprising container 100 in a perspective view.

As required, detailed embodiments of the present invention are disclosed herein; however, it is to be understood that the disclosed embodiments are merely exemplary of the invention that may be embodied in various forms. The figures are not necessarily to scale, and some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Wherever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited.

The term "about" when used in connection with a numerical value refers to the actual given value, and to the approximation to such given value that would reasonably be inferred by one of ordinary skill in the art, including approximations due to the experimental and or measurement conditions for such given value.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Any discussion of the prior art throughout the specification should in no way be considered as an admission that such prior art is widely known or forms part of common general knowledge in the field.

It is an object of the present invention to overcome or ameliorate at least one of the disadvantages of the prior art, or to provide a useful alternative.

The present invention relates to protecting a surgically removed tissue sample from contamination, damage, or loss during a medical procedure by placing the medical tissue sample in a sterile container with distinguishing characteristics and a closure device, in some embodiments. In one application, said medical tissue sample is the cranial bone flap removed during a craniotomy. Any suitable tissue sample can be temporarily stored, according to various embodiments of the present invention. For example, bone, cartilage, skin, muscle, tendon, entire organs or a portion thereof, a vein, an artery, a nerve, and combinations thereof that have been harvested for a graft can be stored until transplanted to the surgical site. Facial features such as ears and noses, teeth, fingers, toes, limbs and portions thereof can be protected in certain embodiments. A tissue sample also can be stored temporarily in certain containers of the present invention, transported, and then transplanted into a different patient. Although the invention is not limited to use during a craniotomy, and the container is not limited to a specific shape, this procedure will be used in the detailed description to follow, to illustrate a device of the invention and its use.

As stated above, certain embodiments of the present invention relate to a container for storing a tissue sample or implantable medical device during a medical procedure, the container comprising: a frame defining a plurality of retention compartments, each retention compartment having an orientation and comprising sidewalls supported by the frame; wherein the sidewalls define a rim for each retention compartment in the plurality of retention compartments; wherein the orientation of a first retention compartment in the plurality of retention compartments differs from the orientation of a second retention compartment in the plurality of retention compartments. The container may further comprise a plurality of lids, one lid for each retention compartment in the plurality of retention compartments; wherein each lid in the plurality of lids comprises a seal adapted to impermeably engage the rim of a retention compartment in the plurality of retention compartments; and an anchor permanently affixing the lid to the frame proximal to the retention compartment in the plurality of retention compartments.

Sidewalls, as used herein, refer to any surface within a retention compartment other than the lid or its seal. A retention compartment can have sidewalls of any suitable geometry. In some cases, a bottom sidewall can form a floor of the retention compartment. In other cases, the sidewalls have such geometry that no surface could properly be called a "floor." In still further cases, the sidewalls define a rim for the retention compartment. The seal of a lid then impermeably engages the rim to close the retention compartment.

Retention compartments have an orientation. As used herein, the orientation of a retention compartment indicates a positioning of the container such that contents of the retention compartment will not pour or fall out if the orientation is "up" and the lid is open. The orientation of two retention compartments can be parallel or they can differ by any desirable angle. In some cases, the orientation of a first retention compartment is least 30 degrees, at least 45 degrees, at least 60 degrees, at least 90 degrees, at least 120 degrees, at least or about 180 degrees from the orientation of a second retention compartment in the plurality of retention compartments of a container.

In some cases, for example, the container comprises one or more polymer materials. Any suitable material can be used for the various parts of the container, such as, for example, polystyrene, polyethylene, polypropylene, polyurethane, nylon, silicone, and combinations thereof. Those materials can be alike, different, or a combination thereof, with some components being made from the same materials, while other components differ. In some cases, for example, the container comprises one or more sustainable materials. Any suitable recycled material can be used, such as, tree pulp, compressed paper, fabric, plastic and combinations thereof. In further cases these recycled materials, as listed above, would receive a watertight finish to ensure suitability for a surgical environment.

The retention compartments receive and store the tissue sample(s) and/or implantable device(s) during the surgical procedure. Generally speaking, the retention compartments represent the inside of the container, and thereby protect and maintain the tissue sample(s) or implantable medical devices. The rim of the retention compartment can be of any suitable configuration, so that the associated lid can impermeably enclose the retention compartment. In some cases, this is done with a seal on the lid engaging the rim of the retention compartment wherein friction between the seal and the rim create an impermeable closure for the retention compartment. In certain cases, at least one rim of a retention compartment in the plurality of retention compartments comprises at least one negative rim structure, for example a depression or hole, for engaging a lid that comprises at least one positive lid structure, for example a pin. The pin fits into the depression or hole, and the engagement between the pin and the hole guides the engagement between seal and the rim, and further maintains that engagement via friction between the pin and the hole, for example. The precise structures of the seal and the rim are not significant, so long as they engage, and enclose the tissue sample.

The lid of each retention compartment being permanently affixed to the frame, or possibly to the rim in some cases, allows separate access to each retention compartment to be opened and closed as desired, in certain instances. The lid can be permanently affixed to the rim of a retention compartment by an anchor; wherein the anchor comprises a rivet having a first end joined to a second end by a shaft, and that shaft defines an axis about which each lid can freely rotate. A rivet useful as an anchor can include any suitable material. In some cases, a rivet comprises a polymer material, a metal material, or a combination thereof. Certain instances provide a polymer material for an anchor comprising polystyrene, polyethylene, polypropylene, polyurethane, nylon, silicone, or a combination thereof. As used herein, an anchor is any suitable structure for attaching a lid to a container such as the rim.

Further instances of the present invention provide a container that can be rotated along the X axis, the Y axis, or Z axis, or a combination of at least two thereof, to grant access to at least one retention compartment in the plurality of retention compartments. As used herein, the X axis and the Y axis meet at a 90 degree angle and are parallel to the horizontal. The Z axis is vertical or perpendicular to the horizontal. For example, a container can be placed on a horizontal surface, such as a surgical table, with the container orientated so two smaller retention compartments are accessible in the present orientation. However, a third retention compartment is available to the user if the container were to be rotated 180 degrees along this same surface, effectively inverting the "bottom" of the container to the "top" and the "top" of the container to the "bottom." In this example, the retention compartments are at a 180 degree angle to one another; however in certain embodiments, one or more retention compartments may be at a 90 degree angle to one another, effectively allowing the container rotation to be 90 degrees to ensure accessibility. Additionally, the container may not need to be rotated at all to access the retention compartments at a 90 degree angle to one another, depending on the preference of the surgical team using the container.

It can be beneficial, in certain instances, for the container to comprise a transparent material, such as for example, glass or transparent polymer, so that the contents of the container can be readily identified without opening the container and risking contamination of the tissue sample. Accordingly, the retention compartments, the lids, or both, in addition to any other part of the container, can be made of or comprise transparent material. In other instances, the container can comprise a translucent material, such as for example, frosted glass or translucent polymer, so that the contents of the container can be identified or at least visualized without opening the container and risking contamination of the tissue sample(s). Accordingly, the retention compartments, the lids, or both, in addition to any other part of the container, can be made of or comprise translucent material.

Sometimes, the container is sterile when it is presented for use in an operating room or other suitable context. Sterilization can occur according to any suitable procedure. For example, sterile manufacture can employ clean rooms, cleaned or purified starting materials, sustained high temperatures sufficient for killing microbes, and combinations thereof to improve the cleanliness or even sterilize the container.

Further instances of the present invention provide a container comprising at least one distinguishing feature. A problem in an operating room or an emergency room when a tissue sample is set aside relates to the identification of that tissue sample's location. Accordingly, certain embodiments of the present invention provide a container readily identifiable as the location of the tissue sample. Any suitable distinguishing feature can be used. Some containers comprise at least one distinguishing feature chosen from: color, label, shape, and combinations thereof. Color can be associated with the container through any suitable means, such as, for example, the material used to make the container or a part thereof has a colorant included in the material, such as is known in polymer article manufacture. Or, adhesive labels or tape can impart a color to the container. In addition, the container can have a special surface or an adhesive label affixed thereto so the container can be labeled to identify the contents. Containers of the present invention can have any suitable shape. In some cases, a container having a distinct shape can be used. Suitable shapes include, but are not limited to: polygons, semicircles, stars, cross shapes, flat-bottom bowls, squares, rectangles, spheres, and the like.

It may be desirable to augment the engagement of the lid with a seal. A seal engaging the rim of each retention compartment may further protect the tissue sample by avoiding accidentally knocking the tissue sample out of the container should the container fall or be jostled. In certain instances, a tab to better grip the lid in order to open, close and rotate the lid may be desirable, specifically when the seal is impermeably engaged to the rim.

It may be desirable to irrigate the tissue sample(s), in some uses of the containers of the present invention. In one instance, a suitable fluid can be added to the retention compartment before or after placing the tissue sample in said retention compartment. In another instance, the retention compartment can comprise at least one absorbent pad in the retention compartment to receive the tissue sample. Any suitable absorbent pad can be used. For example, gauze, sterile gauze, hydrophilic polyester, and combinations thereof can be used as an absorbent pad. Sometimes, the absorbent pad comprises at least one hydro-swellable polymer, either alone or in combination with other suitable materials. Any suitable hydro-swellable polymer can be used. In some cases, the hydro-swellable polymer is chosen from polyacrylic acid, polyacrylamide, polysaccharide, poly-hydroxypropyl methacrylate, and combinations of two or more thereof.

In some cases, the interior of the retention compartments comprise one or more antimicrobial coatings. Any suitable antimicrobial coatings can be used, alone or in combination. In some cases, the anti-microbial coating is chosen from silver sulfadiazine, silver nitrate, silver halide, silver acid salt, chlorhexidine dihydrochloride, chlorhexidine diacetate, taurolidine citrate solution, copper carbonates, thiabendazole, silver salicylates, and combinations thereof.

Optionally, the interior of the retention compartment comprises an insert treated with a bacteriostatic agent. Any suitable bacteriostatic agent can be used, alone or in combination. In some cases, the bacteriostatic agent is chosen from sulfonamides, tetracyclines, trimethoprim, clindamycin, macrolides and combinations thereof. The bacteriostatic agent or agents can be present in any suitable amount in any suitable composition. In some cases, the bacteriostatic agent is present in an aqueous or non-aqueous composition in a concentration of at least 0.1 mg per liter of composition, and the composition is made to contact the insert so the insert comprises an effective amount of the bacteriostatic agent. The insert can include any suitable materials, such as, for example, gauze, sterile gauze, hydrophilic polyester, at least one hydro-swellable polymer as mentioned above, and combinations thereof. In some cases, an insert treated with a bacteriostatic agent can be used in combination with an absorbent pad. In other cases, the absorbent pad can be treated with at least one bacteriostatic agent, and thereby function as an absorbent pad and a bacteriostatic insert.

Certain embodiments relate to containers having structure that imparts greater stability. For example, some containers can comprise one or more non-skid surfaces on the exterior bottom of the retention compartment. A non-skid surface can cover any suitable portion of the bottom, such as a small portion of the bottom, or most of the bottom. Any suitable non-skid surface can be used, alone or in combination. For example, the material used to make the retention compartment can be designed to include ridges, bumps, or other protrusions that impart a non-skid quality to the container. In other cases, one or more rubber or rubber-like pads can be adhered to the bottom to create the non-skid surface(s). Care may be taken, in some cases, to select a non-skid surface that allows for sterilization of the container without damaging the non-skid surface.

Further embodiments relate to containers having a greater stability against tipping. This can be accomplished by any suitable means. In some cases, the retention compartment comprises a stabilizing structure adjustably affixed to the frame and adapted to stabilize the container in all of the potential orientations of the retention compartments. In other cases, the stabilizing structure is adapted to engage a vertical edge in any of these orientations. The stabilizing structure can consist of a double-sided wing that clasps over a vertical edge when orientated in an upright position. To ensure the stabilizing structure can attach to a range of vertical edges, it is designed to have an adjustable height. This adjustability is achieved by inserting one or more rivets, permanently attached to the container, into one or more slots of the stabilizing structure. This relationship will allow for the necessary vertical movement to occur, while the stabilizing structure remains attached. The addition of a stabilizing structure can occur when the container is molded, or the stabilizing structure can be added once the container has been manufactured. In some cases the stabilizing structure comprises one or more polymer materials. Any suitable material can be used for the various parts of the container, such as, for example, polystyrene, polyethylene, polypropylene, polyurethane, nylon, silicone, and combinations thereof. In other embodiments the stabilizing structure may comprise of a metallic material, such as steel, stainless steel, aluminum, titanium, and combinations thereof.

Additional embodiments relate to methods of storing a tissue sample or an implantable medical device during a medical procedure. One such method comprises obtaining a container as described herein; placing the tissue sample(s) into one or more interior retention compartments of the container; impermeably enclosing the retention compartment(s) of the container; and storing the tissue sample in the container. Impermeably enclosing the interior means that fluid cannot flow into or out of the container. By stopping both air and liquid from entering or leaving the container, the tissue sample(s) is protected from dehydration and unnecessary risk of contamination. Further protection from dehydration of the tissue sample(s) is provided by optionally irrigating the tissue sample(s) before impermeably enclosing the interior. Any suitable fluid can be used to irrigate the tissue sample. For example, in some cases, irrigating comprises contacting the tissue sample with water, saline, sterile water, sterile saline, formalin or a combination thereof.

A tissue sample or an implantable medical device can be stored for any suitable duration. In some cases, the storing occurs in less than twelve hours, less than six hours, or less than three hours. The tissue sample is typically harvested at the beginning of the surgical procedure, and may need to be securely stored for a period of time before being attached to the surgical area. It is also possible for a tissue sample to be surgically or otherwise removed from a patient, temporarily stored in a container of the present invention, and transported, such as for example, from one operating room to another, or from the scene of an accident to an emergency room, or to a pathology lab.

Any suitable tissue sample(s) can be stored in the various embodiments of the present invention. In some cases, the tissue sample comprises bone, cartilage, skin, muscle, tendon, an entire organ, a portion of an organ, a vein, an artery, a nerve, or a combination of any of the foregoing. In other cases, the tissue sample comprises one or more ears, a nose, one or more teeth, one or more fingers, one or more toes, one or more limbs, one or more partial limbs, or a combination of two or more thereof.

Further embodiments of the present invention relate to situations where the tissue sample is returned to the patient. Perhaps the tissue sample has been traumatically injured or amputated. Or, perhaps the tissue sample has been removed from the patient so that underlying tissue and organs can be accessed. In still other situations, for example, tissue from one part of the patient has been removed to be grafted onto another location on or in the patient's body, such as a leg vein graft for use in coronary bypass surgery. Similarly, tissue from a biopsy may need to be stored for further investigation or processed through a pathology department. Also, tissue such as adipose tissue may be removed from one part of the patient to use for breast or facial reconstructive surgery. Accordingly, some instances of the present invention involve storing the tissue sample and then surgically returning the tissue sample to the patient. Any suitable techniques can be used to return the tissue sample to the patient, and those techniques may depend on the nature of the tissue sample, the location to which the sample will be placed, the history of the tissue sample, and other factors. In accordance with the present invention, and in one embodiment thereof, a sterilized container for the short term storage of a removed bone flap during a surgical procedure is provided.

Once a container according to the present invention has been used, any suitable fate can befall the container. In some cases, the container can be disposed of as medical waste, such as, for example, by incineration. In other cases, the container can be autoclaved and reused. In still further cases, the container can be chemically cleaned or sterilized, such as by sodium hypochlorite (bleach). In still further cases, a portion of the container can be conditioned for reuse, while other portions can be recycled or discarded. For example, the frame could be made of a material such as high temperature-tolerant nylon, and the lids could be made of a different material such as a soft, pliant polymer that cannot be autoclaved. The frame could be cleaned with autoclaving or bleach, for example, while the lids can be removed and recycled. In a further example, wherein the frame is made of a metal, such as, for example, medical-grade stainless steel, the frame can be autoclaved and then re-fitted with new sterile lids and a stabilizing structure. In a still further example, the lids can comprise stainless steel with a pliant polymer seal, and the seals can be removed, the lids autoclaved, and new seals provided. In yet another example, polymer-containing portions of the container can be recycled in accordance with conventional technology.

Additional embodiments relate to methods of storing an implantable device during a medical procedure. Perhaps a patient is in need of a surgical implant, for example, a shunt, pump, tube, artificial joint, artificial disc, reconstructive implant, plate, screw, rod, lens or bone morphogenetic protein, or a combination thereof. The implant may be prepared at the beginning of the surgical procedure, and may need to be securely stored for a period of time before being attached or inserted into the surgical area. For example, bone morphogenetic proteins are mixed at the time of need within the surgical procedure. However, if the surgery is extended due to unforeseeable events or the surgeon chooses to add larger or more than one bone morphogenetic protein implant, the security and hydration of the implant can be better managed and extended when placed inside a container, such as described herein.

Further embodiments relate to methods of making a container as described herein. Any suitable methods and materials can be used. In some cases, a method of making a container of the present invention comprises injection molding a polymer material to form the frame. In other cases, a method of making a container comprises adhering a plurality of sidewalls to form the frame. Any suitable method of adhering can be used. For example, sidewalls can be welded, glued, fastened, or a combination thereof. Welding, generally speaking, includes the melting of one or more materials so that they will bond. Gluing employs any suitable adhesive. Fastening requires the use of fasteners such as screws or staples. Of course, certain embodiments require a surgical-grade sterile container, so making the container should take that into account.

Still further embodiments provide a manner in which at least one lid in the plurality of lids can be securely fastened to the container. This securing mechanism can encompass any suitable mechanism. For example, in some cases, a user may quickly and easily secure the accessible-side of the lid to ensure the lid does not easily open exposing the contents of the retention compartments should the seal fail. In some embodiments, this securing mechanism includes a clasp and aperture structure that would securely latch the accessible-side of a lid in the plurality of lids to the container frame. In other embodiments, this securing mechanism includes a strap and buckle mechanism that would securely latch the accessible-side of a lid in the plurality of lids to the container frame. In some embodiments, this securing mechanism relies on the flexibility of the material of a lid to ensure tension is achieved in the fastening of the lid. In still additional embodiments, this securing mechanism includes an adhesive mechanism that would secure the accessible-side of a lid in the plurality of lids to the container frame. An adhesive mechanism would include a ribbon of material with a pressure-sensitive adhesive applied to an area thereon. Once the tissue sample or implantable device is placed in the retention compartment, the pressure-sensitive adhesive can be pressed to the frame to secure the lid. Optionally, the pressure-sensitive adhesive is reusable so the lid can be opened and closed repeatedly. Or, the pressure-sensitive adhesive can have an adhesive strength such that once the lid is closed, the lid cannot be reopened except by focused effort, for example, if a tissue sample were to be transported for transplanting.

DETAILED DESCRIPTION OF THE DRAWINGS

Further embodiments of the present invention can be described by reference to the accompanying drawings.

Figure 2:
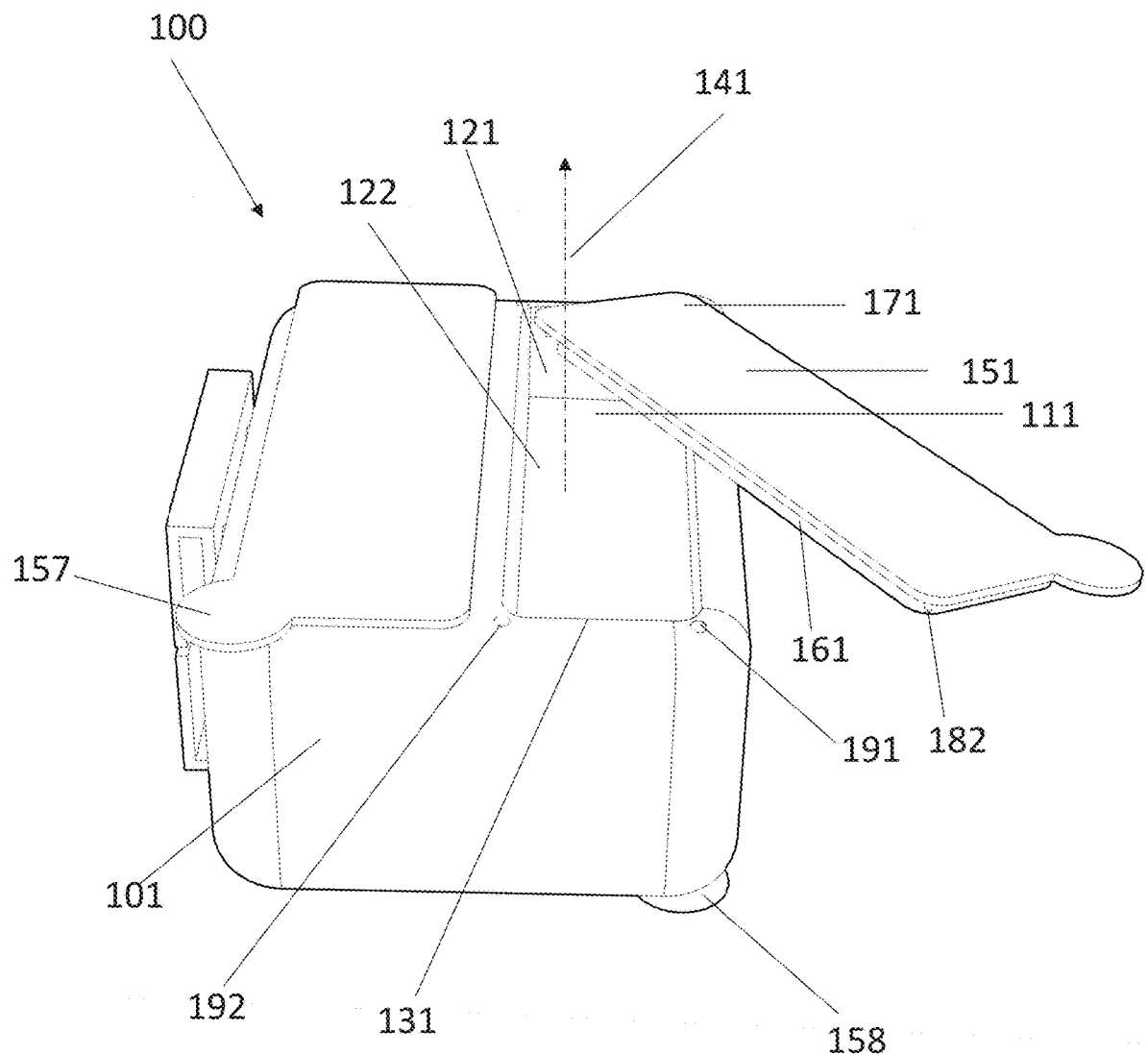
FIG. 2 depicts container 100 in another perspective view with lid 151 opened to reveal retention compartment 111.
Figure 3:
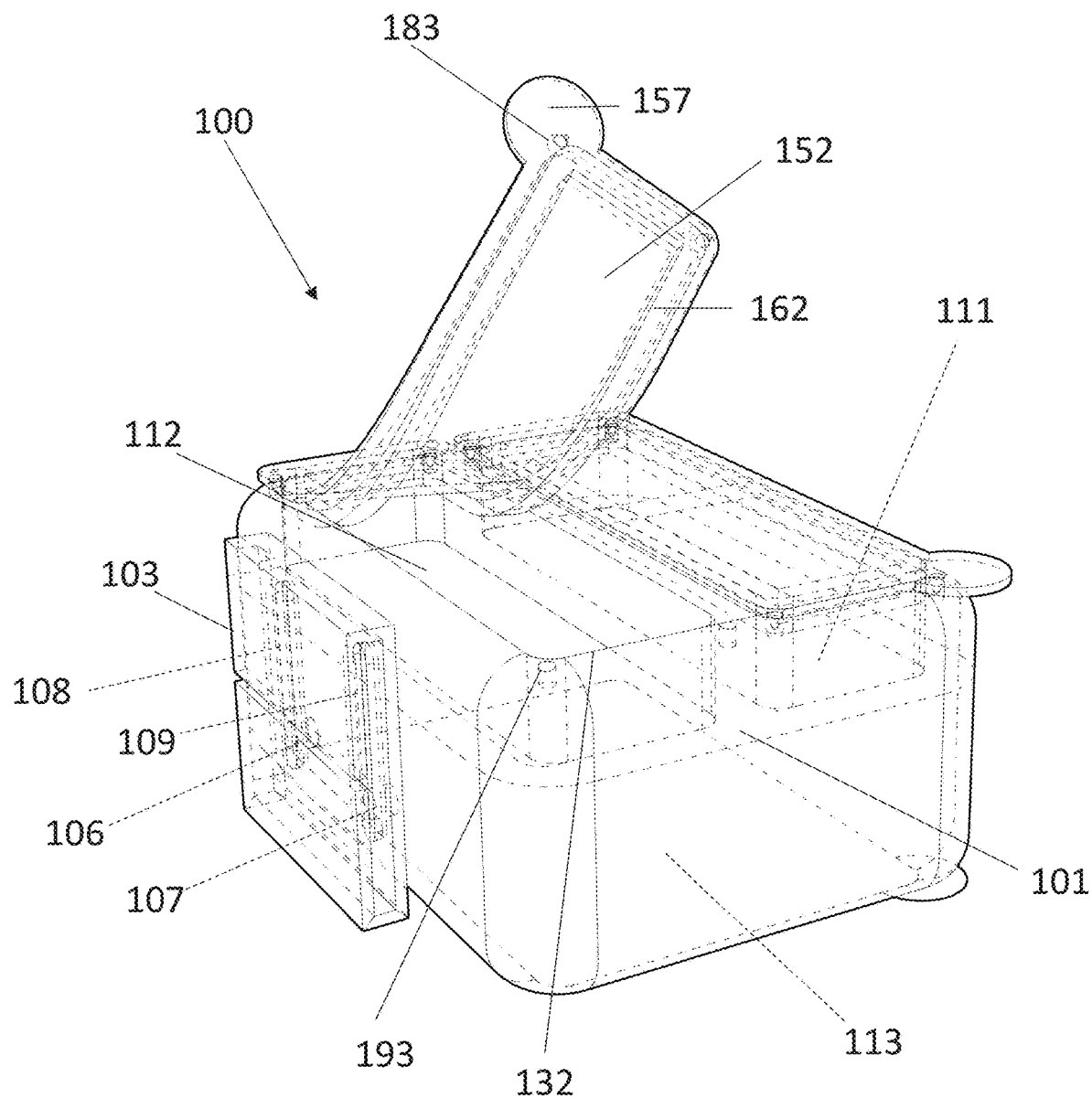
FIG. 3 depicts container 100 in a further perspective view with lid 152 opened to reveal retention compartment 112.
Figure 4:
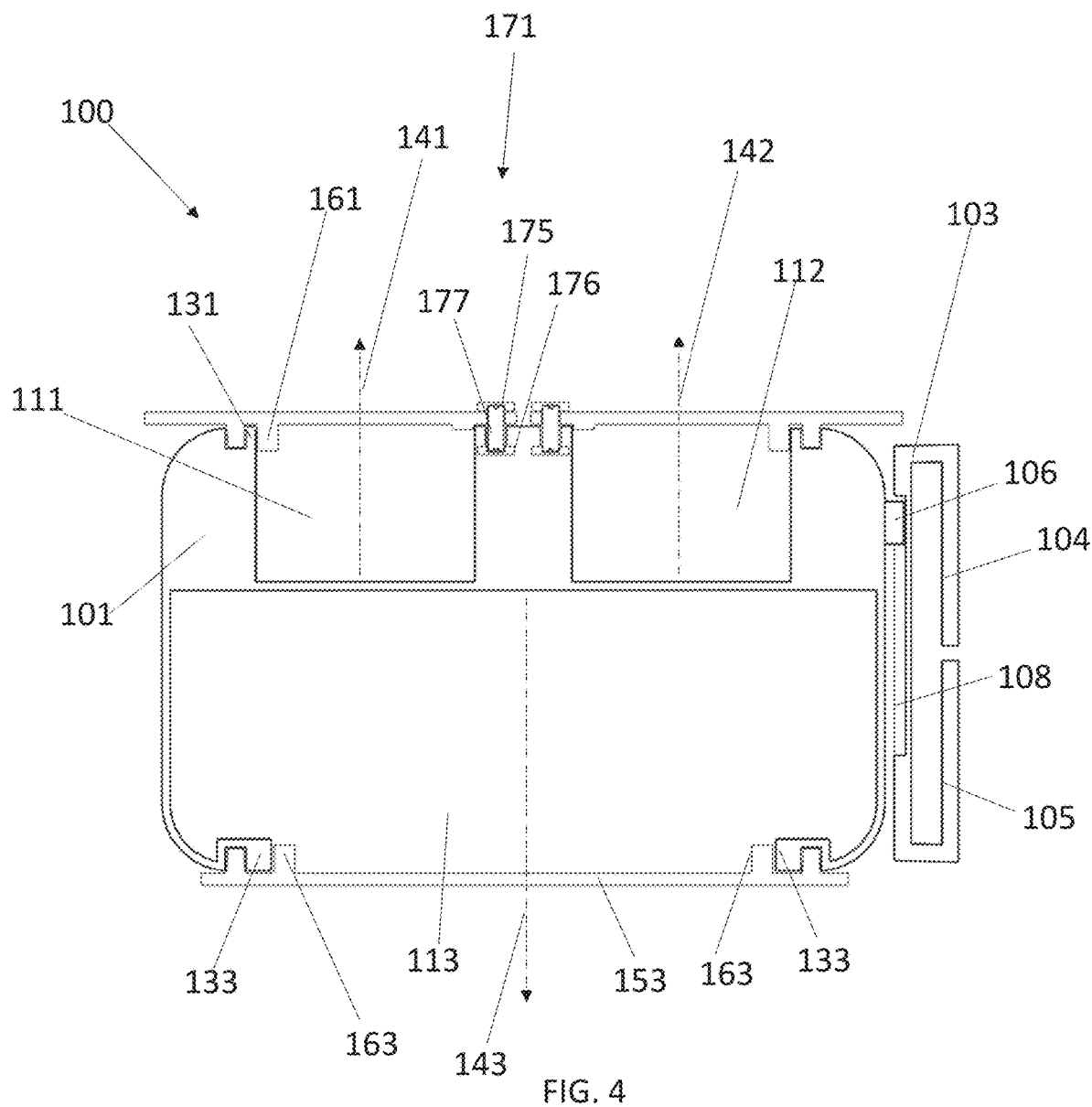
FIG. 4 shows a cut-away elevation view of container 100.
Figure 5:
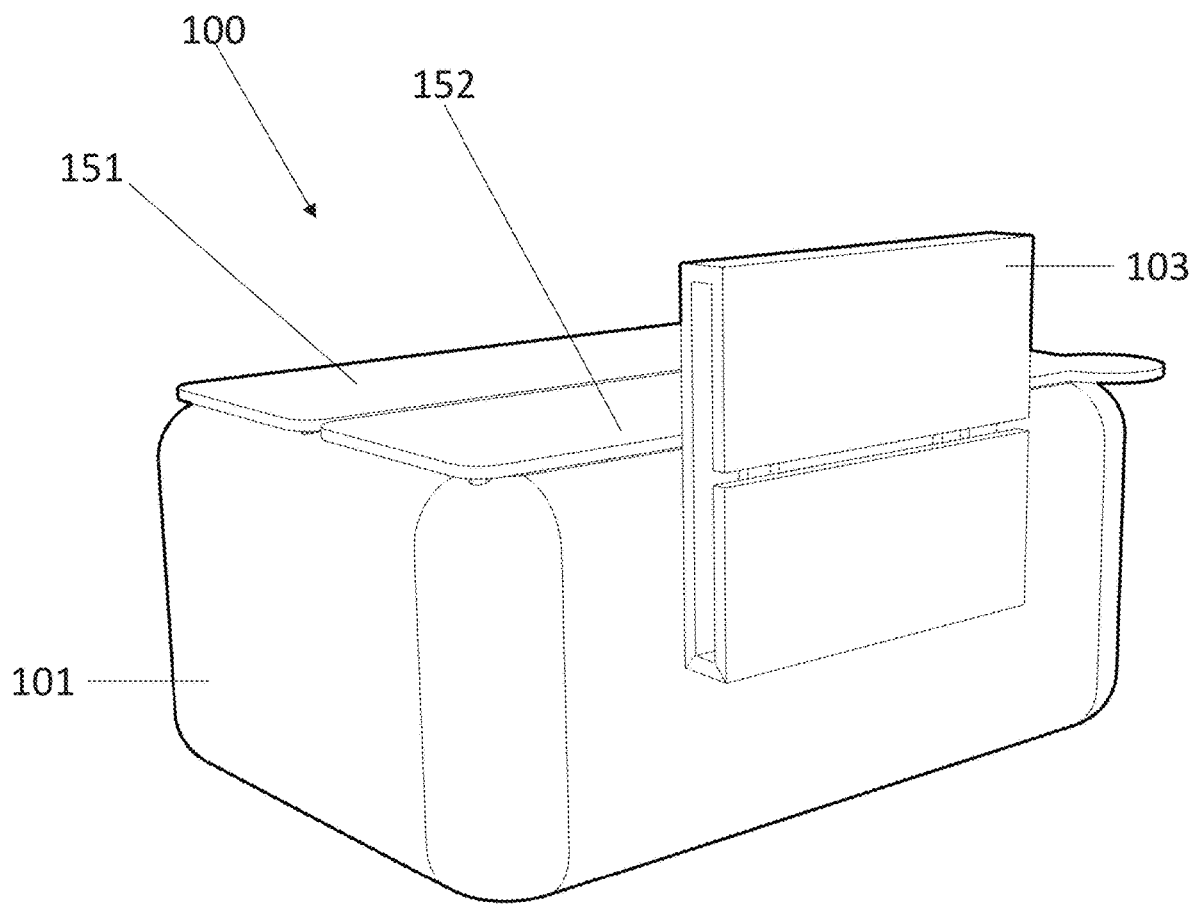
FIG. 5. shows another perspective view of container 100 with stabilization structure 103 adjusted to a different position.
Figure 6:
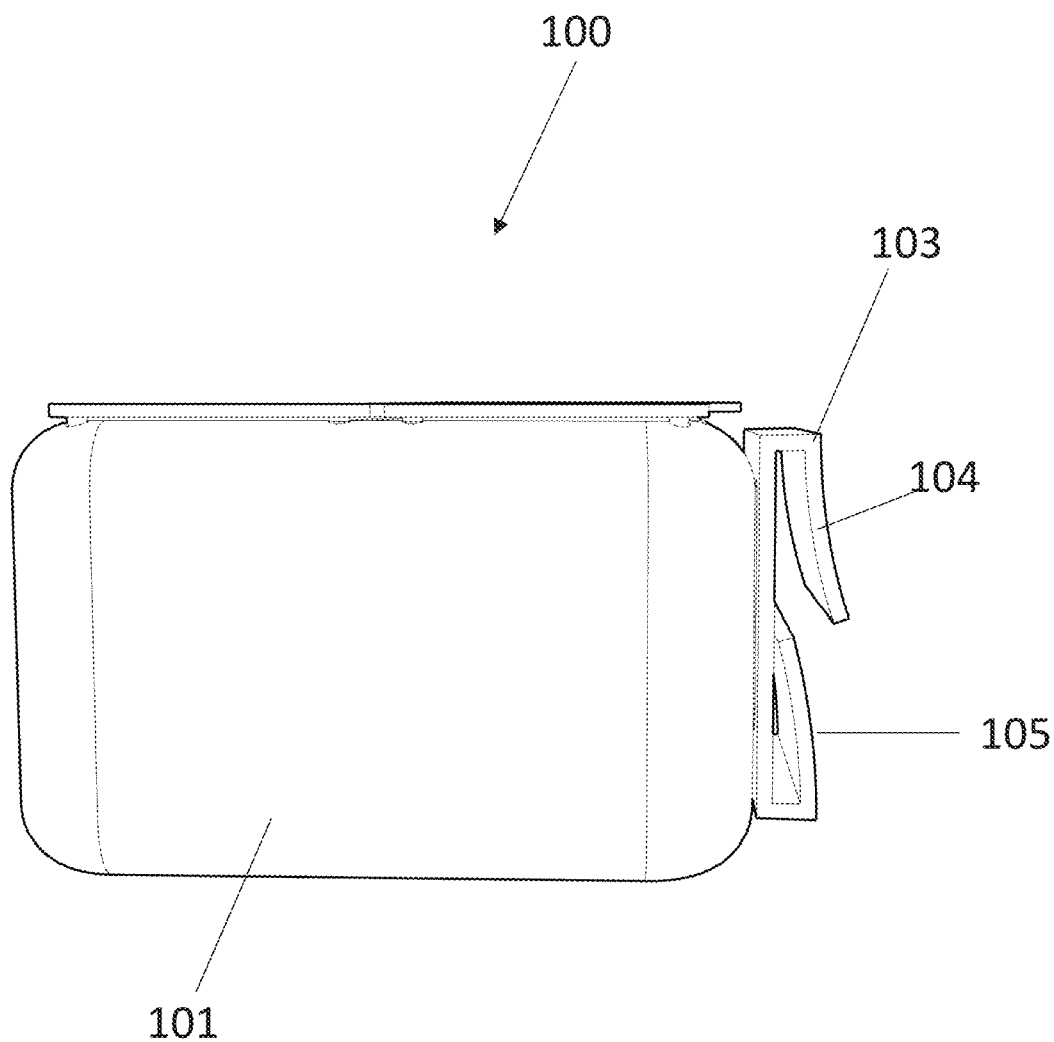
FIG. 6 shows an elevation view of container 100.

FIG. 1 depicts one embodiment of the invention comprising container 100 in a perspective view. In FIG. 2, lid 151 is opened to reveal retention compartment 111. FIG. 3 depicts container 100 in a further perspective view with lid 152 opened to reveal retention compartment 112. FIG. 4 shows a cut-away elevation view of container 100. FIG. 5. shows another perspective view of container 100 with stabilization structure 103 adjusted to a different position, and FIG. 6 further illustrates container 100 with stabilization structure 103.

Container 100, suitable for storing a tissue sample or implantable medical device during a medical procedure, comprises frame 101 that defines a plurality of retention compartments 111, 112, 113, each of which has orientations 141, 142, 143, respectively. Orientations 141, 142 differ from orientation 143 by 180 degrees. Retention compartment 111, for example, comprises sidewall 121 and bottom sidewall 122. Sidewall 121, among others, define rim 131 for retention compartment 111. Container 100 comprises a plurality of lids 151, 152, 153. Lid 151, for example, comprises seal 161 for impermeably engaging rim 131 of retention compartment 111. Lid 151 further comprises anchor 171 that permanently affixes lid 151 to frame 101 proximal to retention compartment 111. Anchor 171 is a rivet having a first end 175 joined to a second end 176 by a shaft 177, wherein the shaft 177 defines an axis about which lid 151 can freely rotate, as seen in FIG. 4. Lid 151 further comprises positive lid structure 182 for engaging rim 131 at negative rim structure 192. Positive lid structure 182 may also be called a pin, and negative rim structure 192 may also be called a hole. Negative rim structure 191 is visible in FIG. 2. Lid 151 further comprises grip 156 for unsealing lid 151. Similarly, lid 152 comprises grip 157; lid 153 comprises grip 158.

Lid 152 comprises seal 162 adapted to impermeably engage rim 132 of retention compartment 112. Positive lid structure 183 on lid 152, and corresponding negative rim structure 193, appear in FIG. 3. Lid 153 comprises seal 163 adapted to impermeably engage rim 133 of retention compartment 113, as seen in FIG. 4.

Stabilizing structure 103 is adjustably affixed to frame 101 and is adapted to stabilize container 100 in orientations 141, 142, which are parallel, and orientation 143, which is inverse. In other words, stabilizing structure 103 can hold container 100 so that retention compartments 111, 112 are "up," or so that retention compartment 113 is "up." In this way, a medical team using container 100 can choose how to stabilize container 100 depending on whether two smaller retention compartments or one larger retention compartment is needed. Stabilizing structure 103 comprises wings 104, 105 that can engage a vertical edge (not shown). The flexibility of wings 104, 105 is illustrated in the elevation view of container 100 in FIG. 6. Stabilizing structure 103 further comprises first slot 108 and second slot 109 that engage rivets 106, 107, respectively, to allow the stabilizing structure 103 to be adjustably attached to the container 100. FIG. 5 shows stabilizing structure 103 in a different position. Rivets 106, 107 (see FIG. 3) have moved along first slot 108 (see FIG. 3) and second slot 109 (see FIG. 3) to allow the adjustment to the different position.

Figure 7:
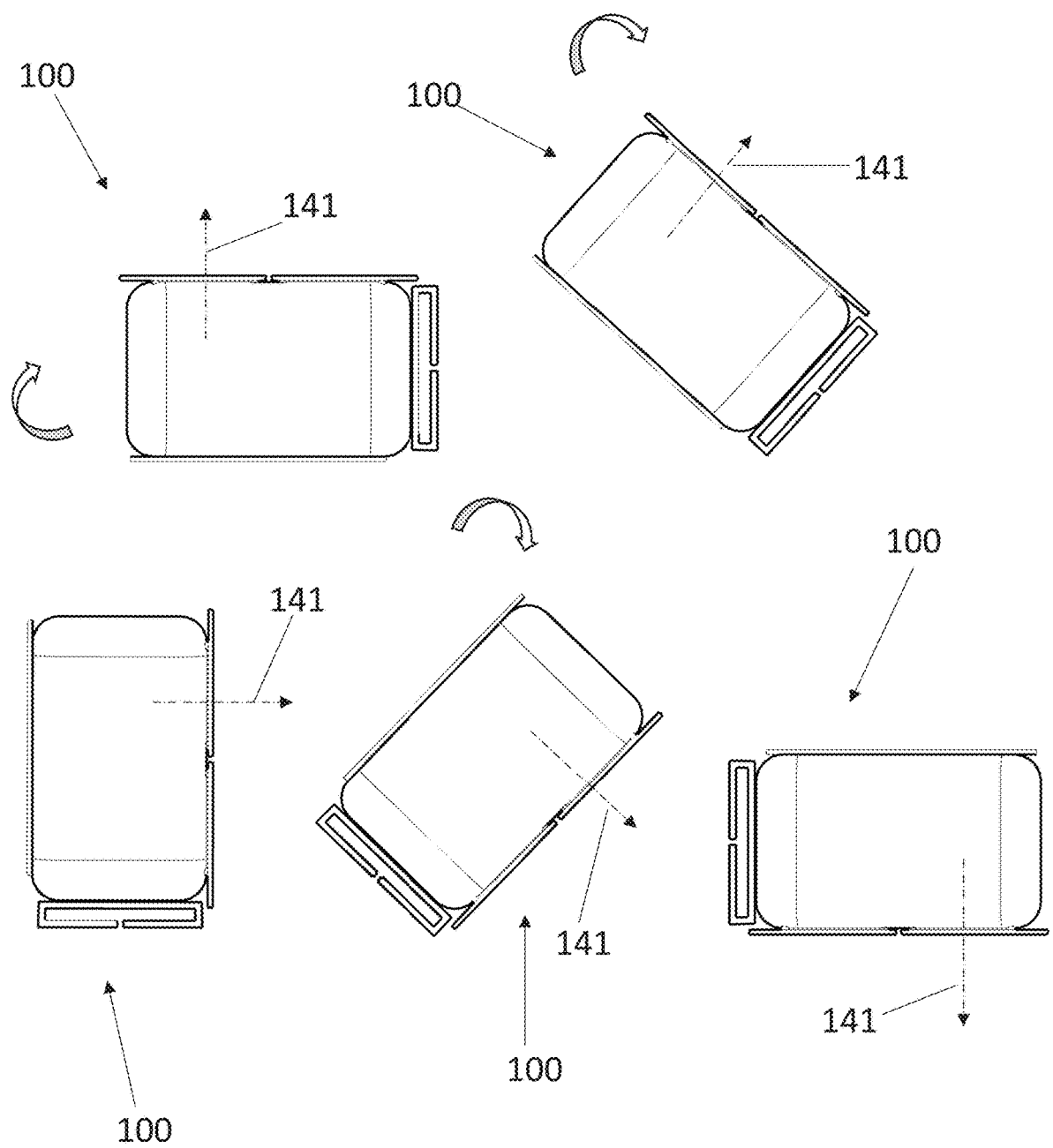
FIG. 7 illustrates rotation of container 100.

FIG. 7 illustrates rotation of container 100, which allows access to retention compartments 111 and 112 with their orientations 141 and 142 pointing "up". Or by rotating container 100 by 180 degrees, retention compartment 113 and corresponding orientation 143 can point "up" and be accessed by a medical team.

Figure 8:
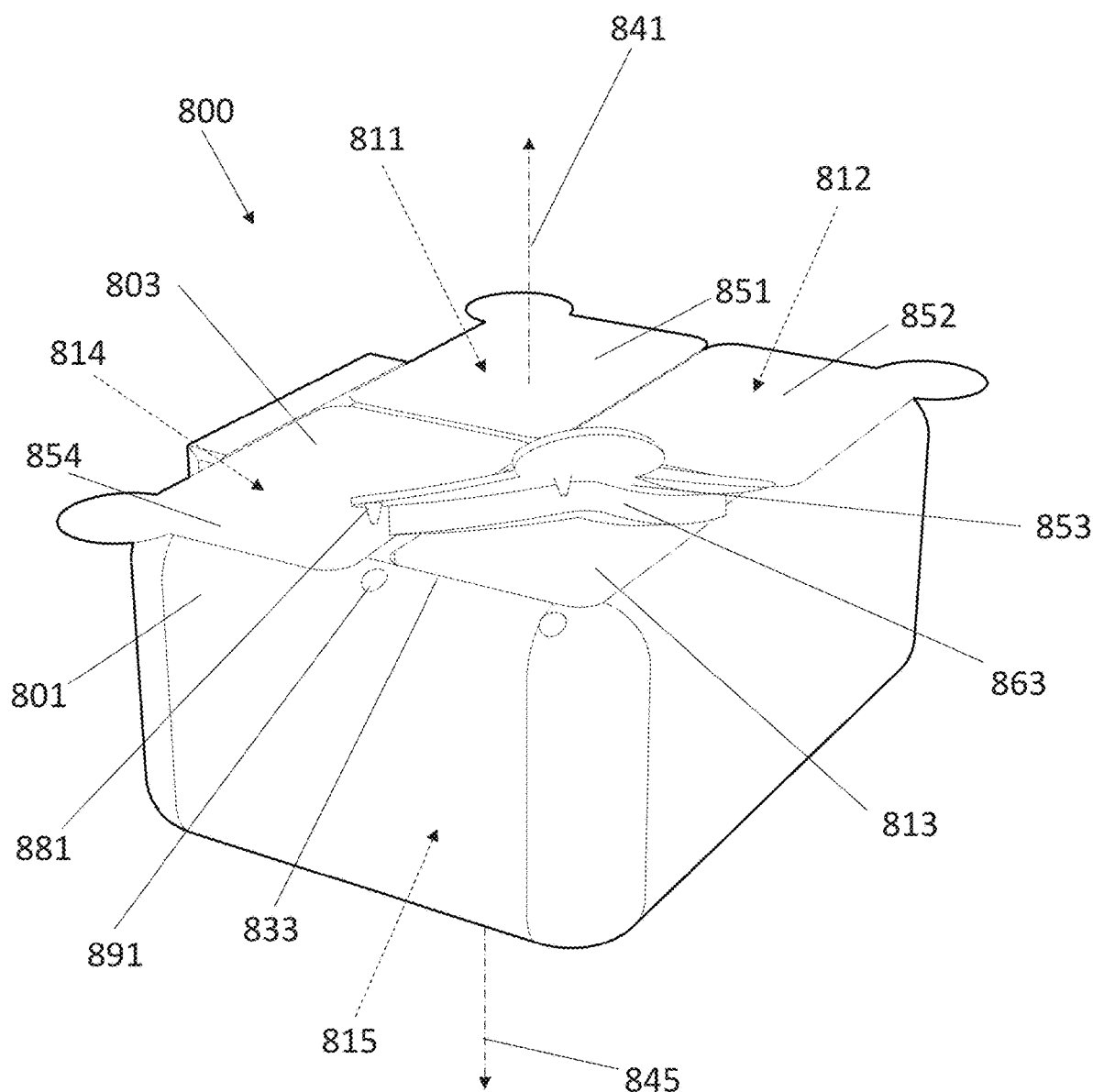
FIG. 8 depicts another embodiment comprising container 800.

FIG. 8 depicts another embodiment comprising container 800. Container 800, suitable for storing a tissue sample or an implantable medical device during a medical procedure, comprises frame 801 and a plurality of retention compartments 811, 812, 813, 814, 815. Retention compartment 811 has an orientation 841 that differs from orientation 845 of retention compartment 815 by 180 degrees. Lids 851, 852, 853, 854 appear in FIG. 8, and lid 855 appears in FIG. 9. Lid 853 comprises seal 863 adapted to impermeably engage rim 833 of retention compartment 813. Lid 853 further comprises positive lid structure 881 for engaging rim 833, which in turn comprises negative rim structure 891 for receiving positive lid structure 881. Container 800 also comprises stabilizing structure 803. As can be seen in the figures, container 800 has further features similar to those seen in container 100.

Figure 9:
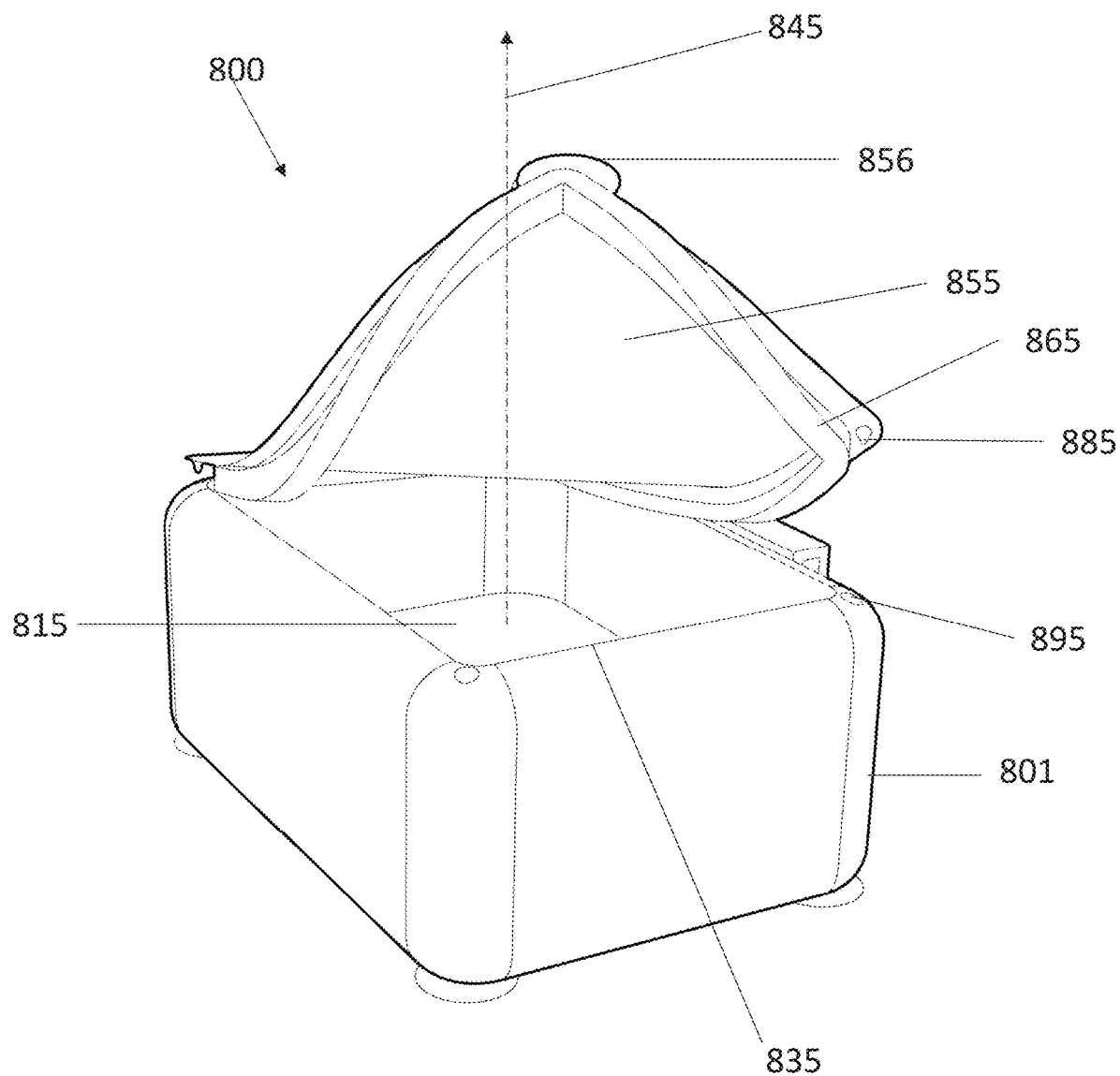
FIG. 9 shows container 800 in a perspective view with lid 855 opened to reveal retention compartment 815.

FIG. 9 shows container 800 in a perspective view with lid 855 opened to reveal retention compartment 815. Lid 855 comprises seal 865 adapted to impermeably engage rim 835 of retention compartment 815, and grip 856 for unsealing lid 855. Lid 855 further comprises positive lid structure 885 that fits into negative rim structure 895.

Figure 10:
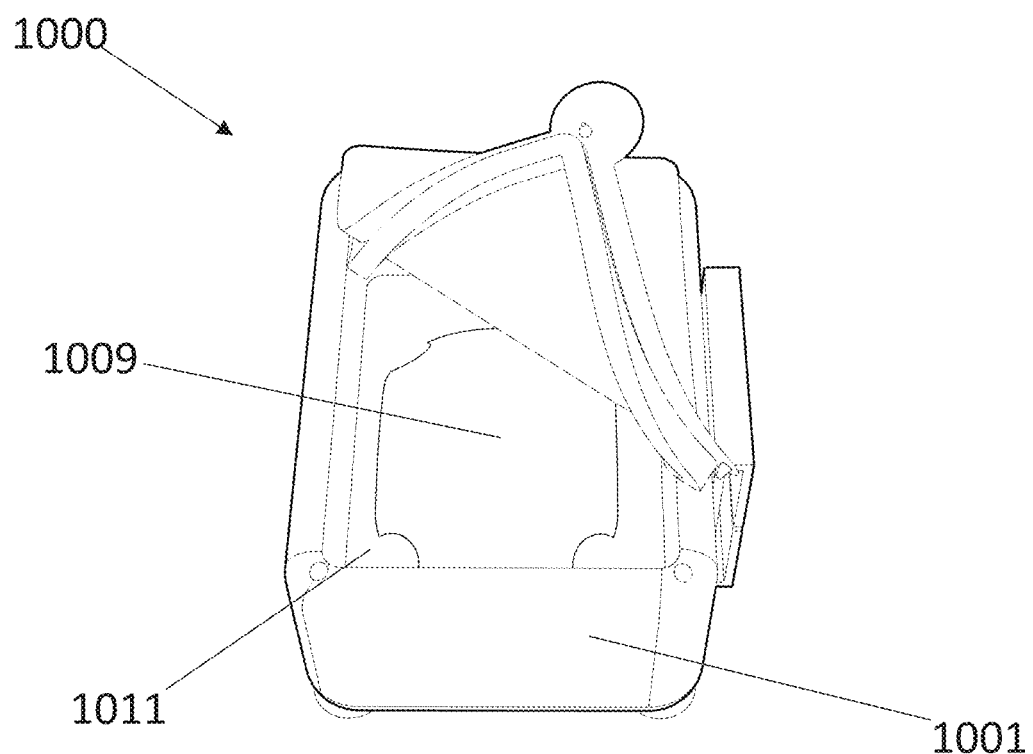
FIG. 10 shows container 1000 having a cranial bone flap 1009 stored therein.

FIG. 10 shows container 1000 having a cranial bone flap 1009 stored therein. Container 1000 is similar to container 800, and comprises frame 1001 and retention compartment 1011. Within retention compartment 1011, a cranial bone flap 1009 can be seen. Cranial bone flap 1009 is being stored during a medical procedure, and will be surgically returned to the patient during that procedure.

Figure 11:
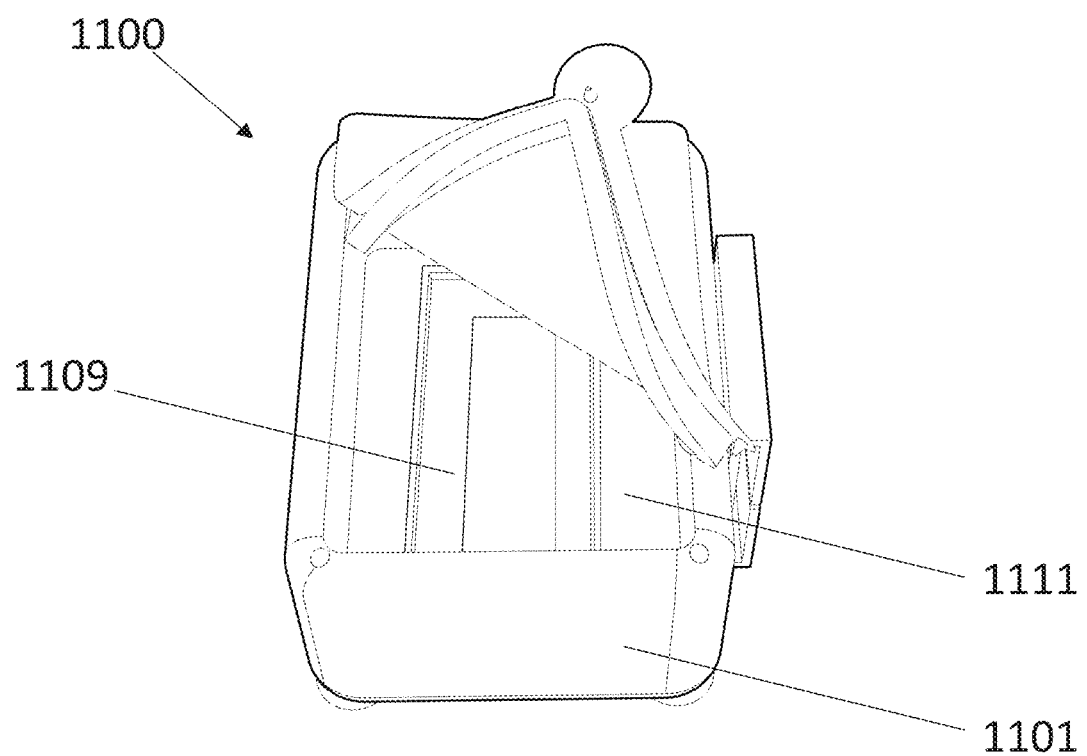
FIG. 11 shows container 1100 having a bone morphogenetic protein implant stored therein.

FIG. 11 shows container 1100 having a bone morphogenetic protein implant 1109 stored therein. Container 1100 is similar to containers 800, 1000, and comprises frame 1101 and retention compartment 1111. Bone morphogenetic protein implant 1109 is being stored within retention compartment 1111 during a medical procedure in which implant 1109 will be surgically placed within a patient.

Figure 12:
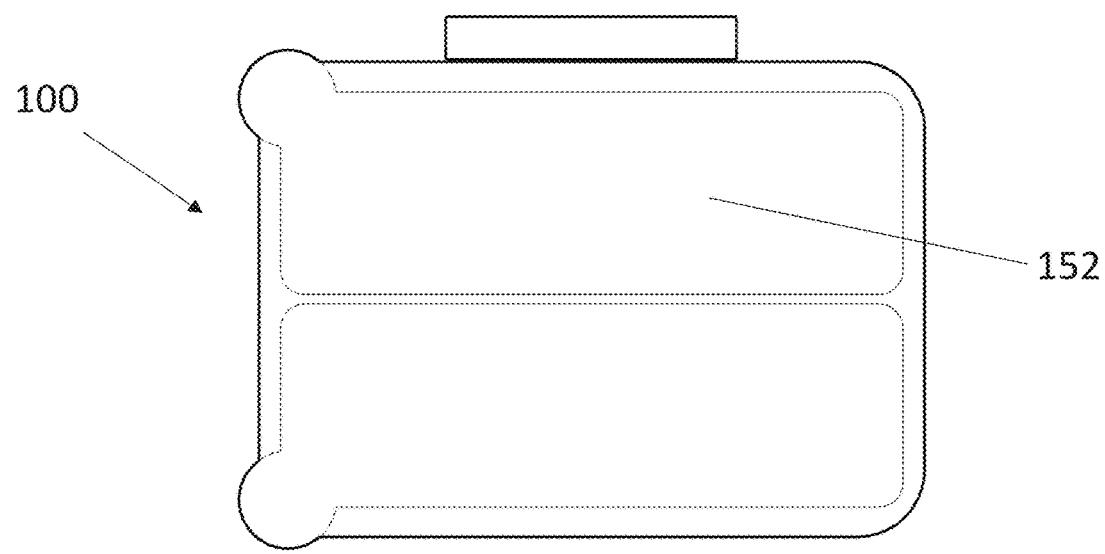
FIG. 12 shows a "top" plan view of container 100.

FIG. 12 shows a "top" plan view of container 100. Lid 152 is labeled to aid the viewer's orientation. As used herein, "top" and "bottom" are completely arbitrary, since the containers described herein can be rotated to any desired position.

Figure 13:
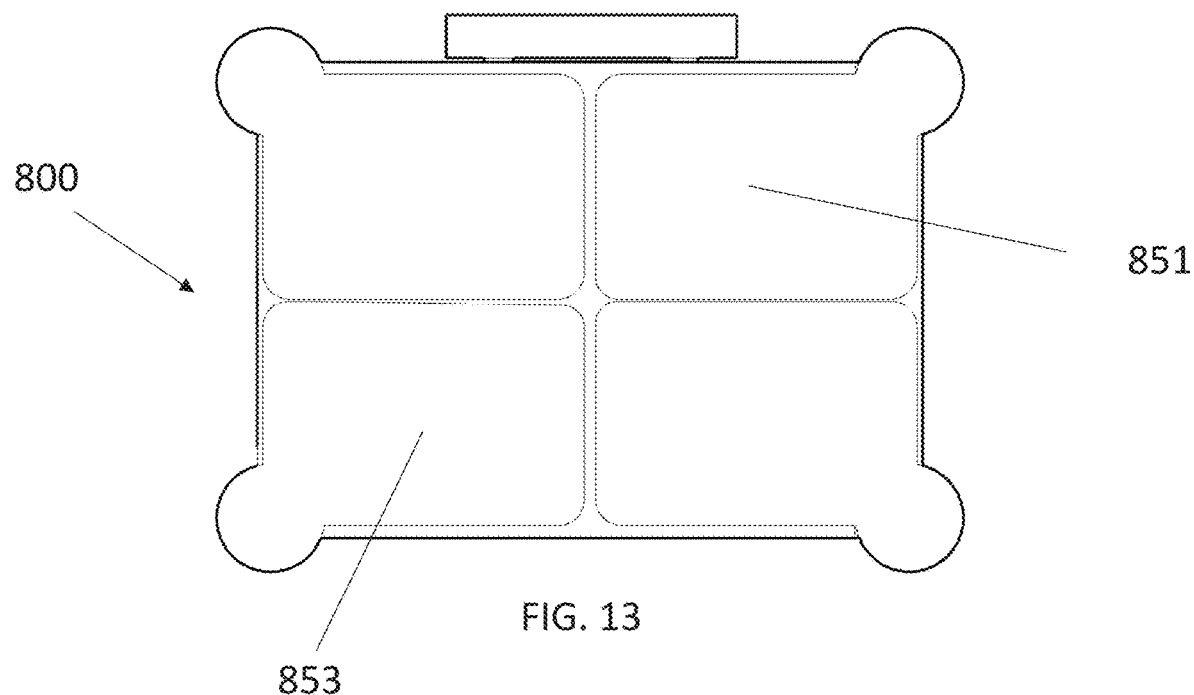
FIG. 13 shows a "top" plan view of container 800.

FIG. 13 shows a "top" plan view of container 800. Lids 851, 853 are labeled to aid the viewer's orientation.

Figure 14:
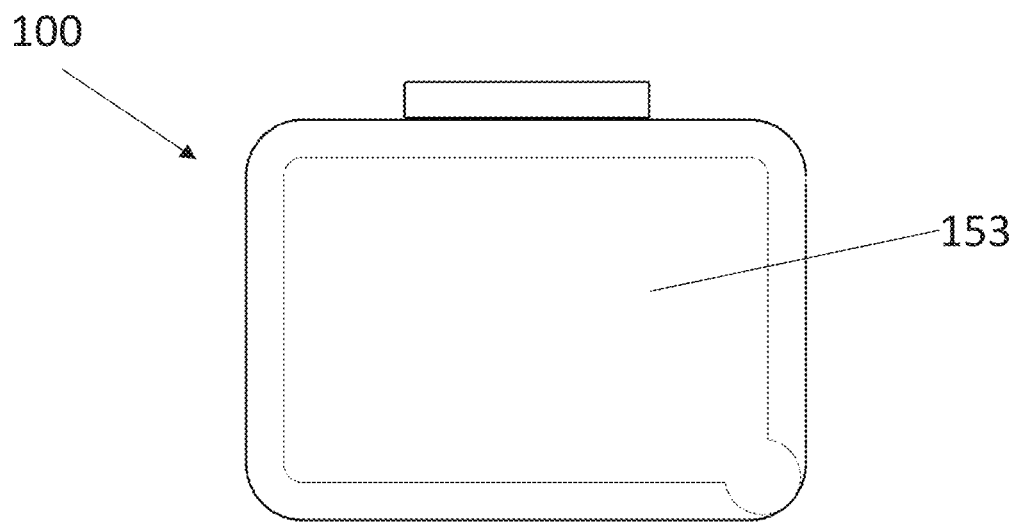
FIG. 14 shows a "bottom" plan view of container 100.

FIG. 14 shows a "bottom" plan view of container 100. Lid 153 is labeled to aid the viewer's orientation.

Figure 15:
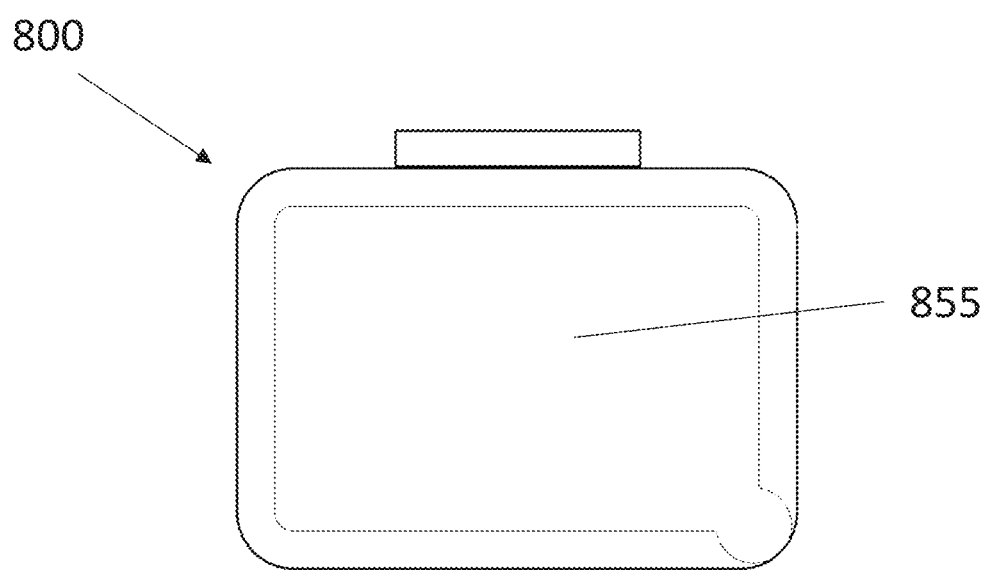
FIG. 15 shows a "bottom" plan view of container 800.

FIG. 15 shows a "bottom" plan view of container 800. Lid 855 is labeled to aid the viewer's orientation.

Figure 16:
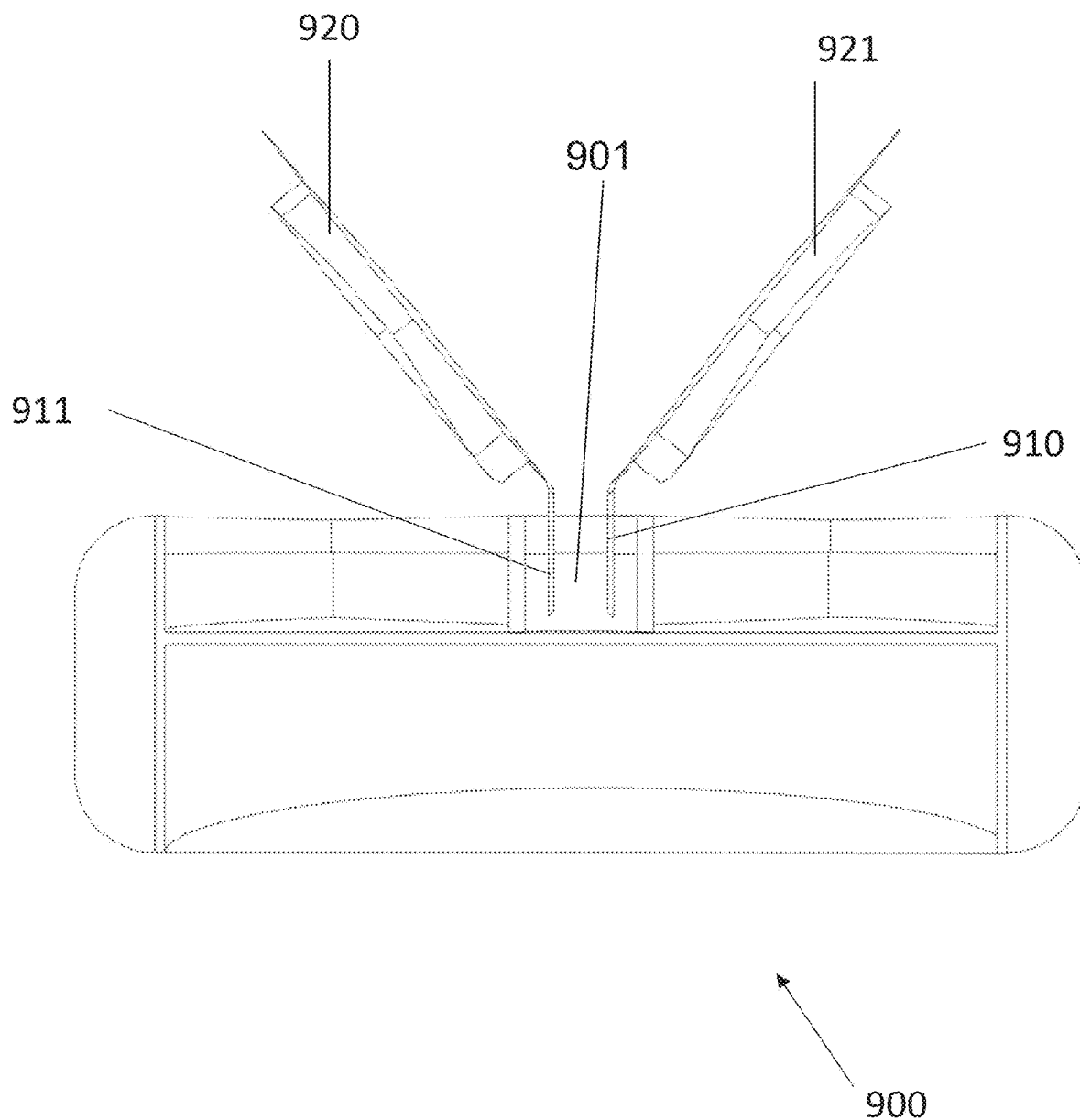
FIG. 16 shows a cut-away elevation view of container 900.

FIG. 16 shows container 900 in a cut-away elevation view with lids 920 and 921 permanently attached to container 900 by embedding tabs 910 and 911 into the frame 901 of container 900.

Figure 17:
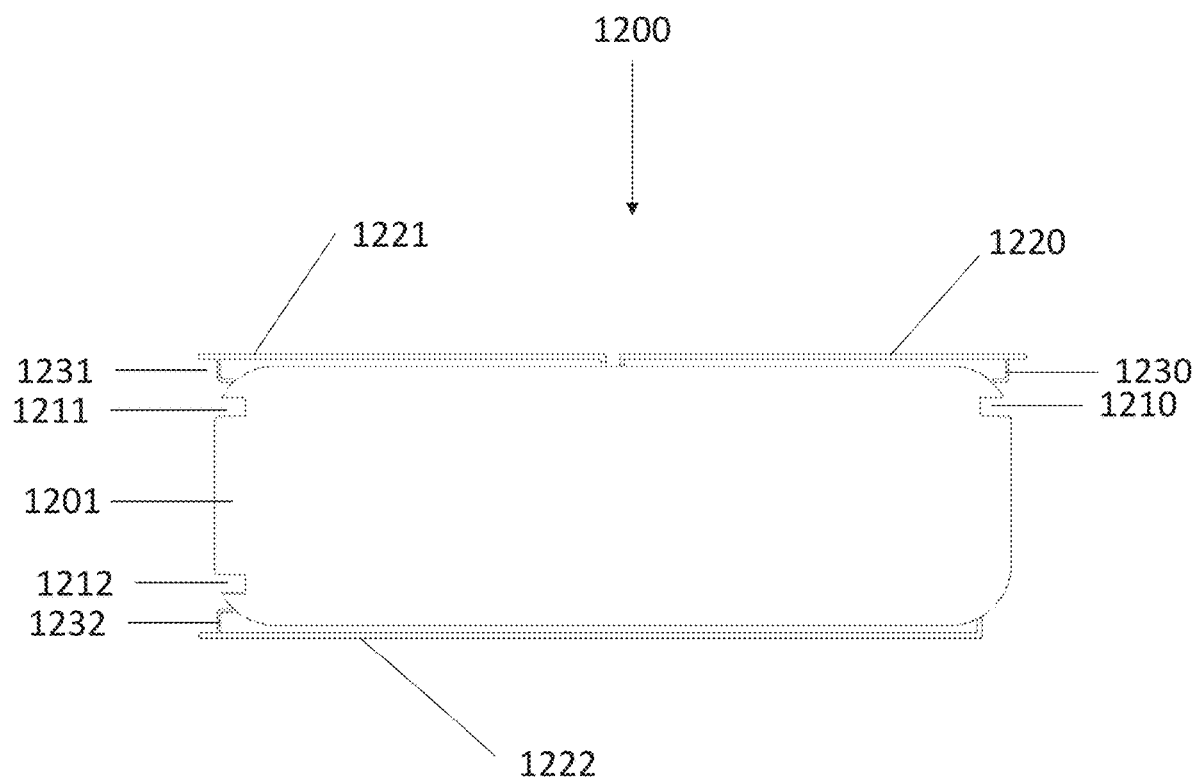
FIG. 17 depicts another embodiment of the invention comprising container 1200 in an elevation view.

FIG. 17 depicts container 1200 in an elevation view. Container 1200, suitable for storing a tissue sample or an implantable medical device during a medical procedure that requires added security, comprises lids 1220, 1221, 1222. Each lid of container 1200 has clasp mechanisms 1230, 1231, 1232, each of which engages apertures, 1210, 1211, 1212, respectively, to securely fasten lids 1220, 1221, 1222 to container 1200. On lid 1220, for example, clasp mechanism 1230 and aperture 1210 can be said to be a securing mechanism wherein the clasp mechanism 1230 is affixed to lid 1220, and aperture 1210 is present in frame 1201. In FIG. 17, clasp mechanisms 1230, 1231, and 1232 are not secured to apertures 1210, 1211, 1212 yet.

Figure 18:
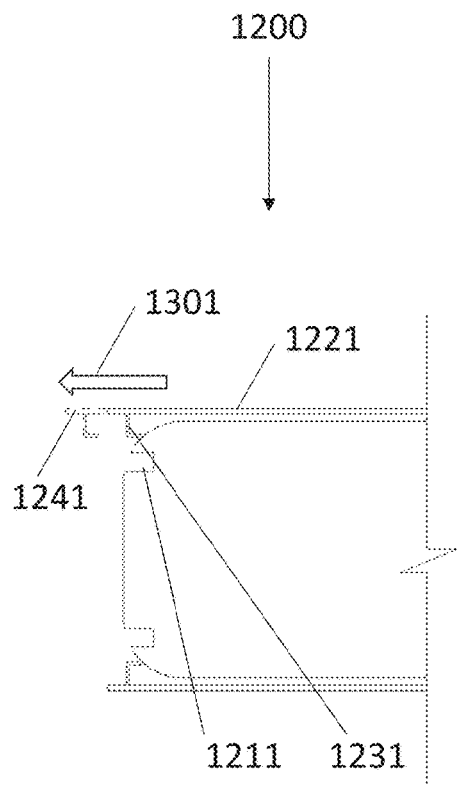
FIG. 18 shows a partial elevation view of container 1200.
Figure 19:
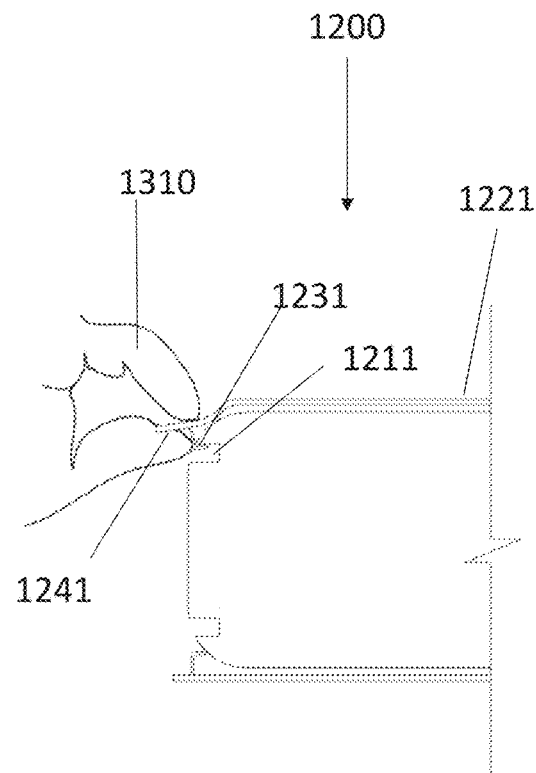
FIG. 19 depicts a partial elevation of container 1200.

FIG. 18 further depicts the securing mechanisms of container 1200 in a cut-away elevation view. Grip 1241 of lid 1221 is manufactured to provide adequate stretch, 1301, to allow for clasp mechanism 1231 to engage aperture 1211. This maneuver can be accomplished by a gloved hand 1310, as seen in FIG. 19, to provide a simple securing mechanism of lid 1221 to container 1200.

EXAMPLES

Example 1—Use of a Container During Craniotomy

A surgical team obtains a container in accordance with the present invention as a necessary tool to appropriately perform a craniotomy. During a craniotomy, a section of the skull, called a bone flap, is removed to access the brain underneath. The skin and muscles are lifted off the bone and folded back, and small burr holes are made in the skull with a drill. A special saw is inserted through the burr holes, and is used to cut the outline of a bone flap. The cut bone flap is lifted and removed to expose the protective covering of the brain called the dura. Once the bone flap is successfully removed by the surgeon, it is then carefully placed inside of the container of the present invention. Prior to this step, a member of the surgical team will prep the container in order to properly receive the bone flap. This is done by orientating the container so the largest retention compartment is facing upwards. Then by grasping the finger grip on the retention compartment's lid, the team member will open the lid to reveal the retention compartment. In some instances, the team member will prepare the retention compartment by adding an adequate amount, but not over filling the retention compartment, with a sterile solution, for example saline, and inserting a laparotomy pad to help retain some of the added solution and add extra padding for the bone flap. The container is then carried over to the patient where the neurosurgeon is ready to place the bone flap inside the retention container. From here, the team member will return the container to the proper surgical table and secure the lid back in place before securing the stability structure to a vertical edge. The container is then left in this position to safely secure the bone flap until the bone flap is needed to attach the necessary titanium plates and screws. Once the bone flap has been prepared for reattachment, the medical team member can return the bone flap to the container in the same manner as previously described. Once the neurosurgeon has repaired of the underlying tissues, the dura is closed with sutures. The bone flap is then returned to the surgeon, possibly via container, before being replaced back in its original position and secured to the skull with titanium plates and screws. The muscles and skin are sutured back together.

Example 2—Use of a Container During a Spinal Fusion

A surgical team obtains a container in accordance with the present invention as a necessary tool to appropriately perform a spinal fusion. During a spinal fusion, particularly an anterior lumbar interbody fusion, a general surgeon will access the patient's spine through the front of their body, pulling the peritoneum and intestinal components to the side to allow access to the spine. A neurosurgeon will then access the lumbar segment that will be fused together. This is done by removing most of the disc material between the two vertebrae segments and replacing it with a fusing material. Once the cavity between the vertebrae segments is prepared, a hollow cage is slid into place. While the neurosurgeon is preparing the vertebrae for fusion, a member of the medical team is preparing the bone morphogenetic protein implant (BMP) that will be placed inside of the hollow cage. Frequently referred to only as BMP, the device that is placed inside of the hollow cage to ensure fusion of the vertebrae consists of a collagen sponge and a BMP-laced liquid. The collagen sponge is packaged in a very shallow tray while the BMP liquid is typically in a syringe. Prior to mixing the two components together, the team member will prep the container of the present invention in order to properly receive the BMP. This is done by orientating the container so the properly sized retention compartment is facing upwards. Then by grasping the finger grip on the retention compartment's lid, the team member will open the lid to reveal the retention compartment. The tray consisting of the collagen sponge is then placed inside of the retention compartment, with the collagen sponge exposed. The BMP solution is then squirted over the top of the collagen sponge to initiate the production of bone. While it is the goal of the medical team to prepare the BMP at the exact right time, in the exact right amount, this may not always be the case. Keeping the mixed solution secure, moist and free of contaminants is important if the BMP is not used immediately upon mixing or saved for a later time within the surgery. To do this, the team member can securely close the lid to the open retention compartment and securely attach the container to a vertical edge by the stability structure. The container is then left in this position to safely secure the BMP until it is needed and fully used.

Example 3—Use of a Container During a Laparotomy

A surgical team obtains a container in accordance with the present invention as a necessary tool to appropriately perform a laparotomy. A laparotomy is commonly performed to investigate abdominal pain or identify the cause of abdominal bleeding. During a laparotomy, a general surgeon makes a vertical incision in the lower abdomen so that underlying organs and tissue can be clearly viewed. Once the surgeon visually inspects the interior of the patient's abdomen, the surgeon may take one or more biopsies from a suspicious area to be studied and identified by a pathologist. In order to properly identify and protect the biopsies, a member of the surgical team will prepare the container to properly receive the biopsies. This is done by orientating the container so the preferred retention compartment is facing upwards; either an orientation exposing a large retention compartment, or an orientation exposing multiple small retention compartments, depending on the size and number of biopsies. Then by grasping the finger grip on the retention compartment's lid, the team member will open the lid to reveal the retention compartment. In some instances, the team member will prepare the retention compartment by adding an adequate amount, but not over filling the retention compartment, with a sterile solution, for example saline, and inserting each biopsy into their own retention compartments. Each retention compartment is then sealed by securely aligning the lid pins with the rim holes and pressing the lid until properly sealed. Each retention compartment is then properly labelled with the patient's corresponding information and any necessary description of the biopsy. From here, the team member may secure the container by clasping the stability structure of the container to a vertical edge, or they may place the container in a sealed hazard bag to be delivered to the hospital's pathology department. If the latter is chosen, a runner will deliver the container, with enclosed and labeled biopsies, to the pathology department where a pathologist will remove each biopsy from its retention compartment to study and identify.

Example 4—Use of a Container During a Traumatic Amputation

A paramedic team obtains a container in accordance with the present invention as a necessary tool to appropriately protect a tissue sample that intends to be surgically returned to the patient. In this instance, a paramedic team is called to the scene of an accident. Upon arriving, they recognize that an individual is injured, the injury resulting in a severed portion of their hand with the loss of one or more extremities, in this case fingers. In order to recover the lost extremities and transport them to the hospital along with the injured individual, a member of the paramedic team will prepare the container to properly receive the extremities. This is done by orientating the container so the preferred retention compartment is facing upwards; either an orientation exposing a large retention compartment, or an orientation exposing multiple small retention compartments, depending on the size and number of extremities. Then by grasping the finger grip on the retention compartment's lid, the team member will open the lid to reveal the retention compartment. In some instances, the team member will prepare the retention compartment by adding an adequate amount, but not over filling the retention compartment, with a sterile solution, for example saline or ice, and inserting each extremity into their own retention compartment. Each retention compartment is then sealed by securely aligning the lid pins with the rim holes and pressing the lid until properly sealed. Each retention compartment is then properly labeled with the individual's corresponding information and any necessary description of contents of each retention compartment. The team member may then choose to place the container and its contents into a refrigeration cabinet to keep it cold. By utilizing the container in accordance with the present invention, the paramedic team can safely transfer the injured individual's extremities with minimal contamination or loss of the tissue sample.

Embodiments

Embodiment 1. A container for storing at least one tissue sample, at least one implantable medical device, or a combination thereof during a medical procedure, the container comprising:
a frame defining a plurality of retention compartments, each retention compartment having an orientation and comprising sidewalls supported by the frame;
wherein the sidewalls define a rim for each retention compartment in the plurality of retention compartments;
wherein the orientation of a first retention compartment in the plurality of retention compartments differs from the orientation of a second retention compartment in the plurality of retention compartments.

Embodiment 2. The container of embodiment 1, further comprising a plurality of lids, one lid for each retention compartment in the plurality of retention compartments;
wherein each lid in the plurality of lids comprises
a seal adapted to impermeably engage the rim of a retention compartment in the plurality of retention compartments;
an anchor permanently affixing the lid to the frame proximal to the retention compartment in the plurality of retention compartments; and
at least part of a securing mechanism for securely closing the lid to the frame.

Embodiment 3. The container of embodiment 2, wherein the securing mechanism comprises a clasp mechanism affixed to the lid and an aperture in the frame.

Embodiment 4. The container of any one of the preceding embodiments, wherein at least one lid in the plurality of lids comprises at least one positive lid structure for engaging the rim of a retention compartment in the plurality of retention compartments, and that rim comprises at least one negative rim structure for receiving the at least one positive lid structure.

Embodiment 5. The container of any one of the preceding embodiments, wherein at least one rim of a retention compartment in the plurality of retention compartments comprises at least one positive rim structure for engaging a lid in the plurality of lids, and that lid comprises at least one negative lid structure for receiving the at least one positive rim structure.

Embodiment 6. The container of any one of the preceding embodiments, wherein at least one lid in the plurality of lids comprises an anchor permanently affixed to the frame of the retention compartment in the plurality of retention compartments.

Embodiment 7. The container of any one of the preceding embodiments, wherein at least one lid in the plurality of lids further comprises at least one grip for unsealing the at least one lid.

Embodiment 8. The container of any one of the preceding embodiments, further comprising a stabilizing structure adjustably affixed to the frame and adapted to stabilize the container in the orientation of at least one retention compartment in the plurality of retention compartments.

Embodiment 9. The container of embodiment 8, wherein the stabilizing structure is adapted to stabilize the container in the orientation of a second retention compartment in the plurality of retention compartments.

Embodiment 10. The container of any one of embodiments 8-9, wherein the stabilizing structure is adapted to stabilize the container in the orientations of all of the retention compartments in the plurality of retention compartments.

Embodiment 11. The container of any one of embodiments 8-10, wherein the stabilizing structure comprises a first polymer material chosen from polystyrene, polyethylene, polypropylene, polyurethane, nylon, silicone, and combinations thereof.

Embodiment 12. The container of any one of embodiments 8-11, wherein the stabilizing structure comprises a metal material chosen from steel, stainless steel, aluminum, titanium, and combinations thereof.

Embodiment 13. The container of any one of embodiments 8-12 wherein the stabilizing structure is adapted to engage a vertical edge.

Embodiment 14. The container of any one of embodiments 8-13, wherein the stabilizing structure has a maximum vertical adjustment of 1.5 times a height of the container.

Embodiment 15. The container of any one of embodiments 8-14 wherein the stabilizing structure comprises:
a first slot and a second slot adapted to receive a first rivet and a second rivet, respectively, to allow the stabilizing structure to be adjustably attached to the container.

Embodiment 16. The container of any one of embodiments 8-15 wherein the stabilizing structure comprises:
a first wing and a second wing adapted to engage a vertical edge in one or more of the orientations of the retention compartments in the plurality of retention compartments.

Embodiment 17. The container of any one of the preceding embodiments, wherein the orientation of the first retention compartment is least 3 degrees, at least 45 degrees, at least 60 degrees, at least 90 degrees, at least 120 degrees, or about 180 degrees from the orientation of the second retention compartment in the plurality of retention compartments.

Embodiment 18. The container of any one of the preceding embodiments, wherein the frame can be rotated along the 'X' axis, 'Y' axis, or 'Z' axis, or a combination of two thereof, to grant access to at least one retention compartment in the plurality of retention compartments.

Embodiment 19. The container of embodiment 17 wherein the frame can be rotated along the 'X' axis, 'Y' axis, or 'Z' axis, or a combination of two thereof, at least 3 degrees, at least 45 degrees, at least 60 degrees, at least 90 degrees, at least 120 degrees, or at least 180 degrees.

Embodiment 20. The container of any one of the preceding embodiments, wherein the frame comprises a second polymer material.

Embodiment 21. The container of embodiment 20, wherein the second polymer material is chosen from polystyrene, polyethylene, polypropylene, polyurethane, nylon, silicone, and combinations thereof.

Embodiment 22. The container of any one of the preceding embodiments, wherein the plurality of lids comprises a third polymer material.

Embodiment 23. The container of embodiment 22, wherein the third polymer material is chosen from polystyrene, polyethylene, polypropylene, polyurethane, nylon, silicone, and combinations thereof.

Embodiment 24. The container of embodiment 22, wherein plurality of lids comprises a transparent material, a translucent material, or a combination thereof.

Embodiment 25. The container of any one of the preceding embodiments, wherein permanently affixing at least one lid to at least one rim of a retention compartment in the plurality of retention compartments comprises using an anchor.

Embodiment 26. The container of embodiment 25, wherein the anchor comprises a rivet having a first end joined to a second end by a shaft, wherein the shaft defines an axis about which the at least one lid can freely rotate.

Embodiment 27. The container of embodiment 26, wherein the rivet comprises a fourth polymer material, a metal material, or a combination thereof.

Embodiment 28. The container of embodiments 25-27, wherein the shaft comprises a fifth polymer material, a metal material, or a combination thereof.

Embodiment 29. The container of any one of the preceding embodiments, wherein the container is sterile.

Embodiment 30. The container of any one of the preceding embodiments, further comprising at least one distinguishing feature chosen from: color, label, shape, and combinations thereof.

Embodiment 31. The container of any one of the preceding embodiments, wherein at least one retention compartment in the plurality of retention compartments is marked with tissue sample identification information within the at least one retention compartment.

Embodiment 32. The container of any one of the preceding embodiments, wherein at least one lid in the plurality of lids is marked with tissue sample identification information.

Embodiment 33. The container of any one of the preceding embodiments, wherein the first polymer material, second polymer material, third polymer material, fourth polymer, and fifth polymer can be alike, different, and combinations thereof.

Embodiment 34. A method of storing a tissue sample during a medical procedure, comprising:
obtaining the container of any one of the preceding embodiments;
placing the tissue sample into a retention compartment in the plurality of retention compartments;
impermeably engaging the seal of a lid in the plurality of lids to the retention compartment containing the tissue sample; and
storing the tissue sample in the container.

Embodiment 35. The method of embodiment 34, further comprising irrigating the tissue sample before impermeably engaging the seal.

Embodiment 36. The method of embodiment 35, wherein the irrigating comprises contacting the tissue sample with water, saline, sterile water, sterile saline, formalin, or a combination thereof.

Embodiment 37. The method of any one of embodiments 34-36, wherein the storing occurs for less than twelve hours.

Embodiment 38. The method of any one of embodiments 34-37, wherein the storing occurs for less than 48 hours.

Embodiment 39. The method of any one of embodiments 34-38, wherein the tissue sample comprises bone, cartilage, skin, muscle, tendon, an entire organ, a portion of an organ, a vein, an artery, a nerve, or a combination of any of the foregoing.

Embodiment 40. The method of any one of embodiments 34-39, wherein the tissue sample comprises one or more ears, a nose, one or more teeth, one or more fingers, one or more toes, one or more limbs, one or more partial limbs, or a combination of two or more thereof.

Embodiment 41. The method of any one of embodiments 34-40, further comprising:
after the storing, surgically returning the tissue sample to the patient.

Embodiment 42. A method of storing an implantable device, prior to or during a medical procedure, comprising:
obtaining the container of any one of the preceding embodiments;
placing the implantable device into a retention compartment in the plurality of retention compartments;
impermeably engaging the seal of a lid in the plurality of lids to the retention compartment containing the implantable device; and
storing the implantable device in the container.

Embodiment 43. The method of embodiment 42, further comprising irrigating the implantable device before impermeably engaging the seal.

Embodiment 44. The method of embodiment 43, wherein the irrigating comprises contacting the implantable device with water, saline, sterile water, sterile saline, antibiotic solution, a protein solution, bacteriostatic insert, or a combination thereof.

Embodiment 45. The method of embodiment 43-44 wherein the storing occurs for less than twelve hours.

Embodiment 46. The method of embodiment 43-44, wherein the storing occurs for less than 48 hours.

Embodiment 47. The method of embodiment 42, wherein the implantable device comprises a shunt, a pump, a tube, an artificial joint, an artificial disc, a reconstructive implant, a plate, a screw, a rod, a lens, a bone morphogenetic protein, or a combination of any of the foregoing.

Embodiment 48. A method of making the container of any one of embodiments 1-47 comprising:
injection molding a second polymer material to form the frame.

Embodiment 49. A method of making the container of any one of embodiments 1-48 comprising:
adhering a plurality of sidewalls to form the frame.

Embodiment 50. The method of embodiment 49, wherein the adhering comprises welding, gluing, fastening, or a combination thereof.

Embodiment 51. The method of any one of embodiments 48-50, comprising:
injection molding a third polymer material to form the at least one lid; affixing the at least one lid to the frame;
Injection molding a first polymer material to form the stabilizing structure; and affixing the stabilizing structure to the frame.

Embodiment 52. The method of any one of embodiments 48-51, further comprising:
permanently affixing at least one lid to at least one rim of a retention compartment in the plurality of retention compartments using an anchor.

Embodiment 53. The method of embodiment 52, wherein the anchor comprises a rivet having a first end joined to a second end by a shaft, wherein the shaft defines an axis about which the at least one lid can freely rotate.

Embodiment 54. The method of embodiment 53, wherein the rivet comprises a fourth polymer material, a metal material, or a combination thereof.

Embodiment 55. The method of embodiment 54, wherein the fourth polymer material comprises polystyrene, polyethylene, polypropylene, polyurethane, nylon, silicone, and combinations thereof.

Embodiment 56. A method of increasing the safety of a patient undergoing a medical procedure, comprising employing the container of any one of embodiments 1-33 to store at least one tissue sample, at least one implantable device, or a combination thereof during the medical procedure.

As previously stated, detailed embodiments of the present invention are disclosed herein; however, it is to be understood that the disclosed embodiments are merely exemplary of the invention that may be embodied in various forms. It will be appreciated that many modifications and other variations stand within the intended scope of this invention as claimed below. Furthermore, the foregoing description of various embodiments does not necessarily imply exclusion. For example, "some" embodiments may include all or part of "other" and "further" embodiments within the scope of this invention. In addition, "a" does not mean "one and only one;" "a" can mean "one and more than one."

We claim:

1. A container for storing at least one tissue sample, at least one implantable medical device, or a combination thereof during a medical procedure, the container comprising:
    a frame defining a plurality of retention compartments, each retention compartment having an up orientation and comprising sidewalls supported by the frame; and
    a stabilizing structure adjustably affixed to the frame and adapted to stabilize the container in the up orientation of at least one retention compartment in the plurality of retention compartments;
    wherein the sidewalls define a rim for each retention compartment in the plurality of retention compartments;
    wherein the up orientation of a first retention compartment in the plurality of retention compartments differs from the up orientation of a second retention compartment in the plurality of retention compartments;
    wherein the stabilizing structure is adapted to selectively stabilize the container in the up orientations of all of the retention compartments in the plurality of retention compartments; and
    wherein the stabilizing structure comprises a first elongated slot receiving a first rivet permanently attached to the container and a second elongated slot receiving a second rivet permanently attached to the container adjustably attaching the stabilizing structure to the container.

2. The container of claim 1, further comprising a plurality of lids, one lid for each retention compartment in the plurality of retention compartments;
    wherein each lid in the plurality of lids comprises
    a seal adapted to impermeably engage the rim of a retention compartment in the plurality of retention compartments;
    an anchor permanently affixing the lid to the frame proximal to the retention compartment in the plurality of retention compartments; and
    at least part of a securing mechanism for securely closing the lid to the frame.

3. The container of claim 2, wherein the securing mechanism comprises a clasp mechanism affixed to the lid and an aperture in the frame.

4. The container of claim 2, wherein at least one lid in the plurality of lids comprises at least one positive lid structure for engaging the rim of a retention compartment in the plurality of retention compartments, and that rim comprises at least one negative rim structure for receiving the at least one positive lid structure.

5. The container of claim 2, wherein at least one rim of a retention compartment in the plurality of retention compartments comprises at least one positive rim structure for engaging a lid in the plurality of lids, and that lid comprises at least one negative lid structure for receiving the at least one positive rim structure.

6. The container of claim 2, wherein at least one lid in the plurality of lids comprises an anchor permanently affixed to the frame of the retention compartment in the plurality of retention compartments.

7. The container of claim 2, wherein at least one lid in the plurality of lids further comprises at least one grip for unsealing the at least one lid.

8. The container of claim 1, wherein the stabilizing structure comprises a first polymer material chosen from polystyrene, polyethylene, polypropylene, polyurethane, nylon, silicone, and combinations thereof.

9. The container of claim 1, wherein the stabilizing structure comprises a metal material chosen from steel, stainless steel, aluminum, titanium, and combinations thereof.

10. The container of claim 1, wherein the stabilizing structure is adapted to engage a vertical edge.

11. The container of claim 1, wherein the stabilizing structure comprises:
a first wing opposing a second wing, so the stabilizing structure is adapted to engage a vertical edge with the first wing selectively orienting the first retention compartment up or engage the vertical edge with the second wing orienting the second retention compartment up.

12. The container of claim 1, wherein the up orientation of the first retention compartment is about 180 degrees from the up orientation of the second retention compartment in the plurality of retention compartments.

13. The container of claim 1, wherein the frame comprises a second polymer material.

14. The container of claim 13, wherein the second polymer material is chosen from polystyrene, polyethylene, polypropylene, polyurethane, nylon, silicone, and combinations thereof.

15. The container of claim 2, wherein the plurality of lids comprises a third polymer material.

16. The container of claim 15, wherein the third polymer material is chosen from polystyrene, polyethylene, polypropylene, polyurethane, nylon, silicone, and combinations thereof.

17. The container of claim 1, wherein the container is sterile.

18. The container of claim 11, wherein the first wing and the second wing are flexible.

* * * * *